(12) United States Patent
Nishimura et al.

(10) Patent No.: US 8,144,993 B2
(45) Date of Patent: Mar. 27, 2012

(54) MEDICAL IMAGE PROCESSING METHOD

(75) Inventors: Hirokazu Nishimura, Hachioji (JP); Jun Hasegawa, Hino (JP); Hideki Tanaka, Hino (JP); Ryoko Inoue, Hachioji (JP); Tetsuo Nonami, Hino (JP)

(73) Assignee: Olympus Corporation, Tokyo (JP)

( * ) Notice: Subject to any disclaimer, the term of this patent is extended or adjusted under 35 U.S.C. 154(b) by 937 days.

(21) Appl. No.: 11/811,263

(22) Filed: Jun. 8, 2007

(65) Prior Publication Data
US 2008/0292154 A1 Nov. 27, 2008

Related U.S. Application Data

(63) Continuation of application No. PCT/JP2005/022562, filed on Dec. 8, 2005.

(30) Foreign Application Priority Data

Dec. 10, 2004 (JP) .................................. 2004-359054
Dec. 13, 2004 (JP) .................................. 2004-360319

(51) Int. Cl.
*G06K 9/48* (2006.01)
*G06K 9/00* (2006.01)
(52) U.S. Cl. .......................... 382/199; 382/128; 382/266
(58) Field of Classification Search .................. 382/128, 382/199, 266
See application file for complete search history.

(56) References Cited

U.S. PATENT DOCUMENTS

| 5,018,509 A | 5/1991 | Suzuki et al. |
|---|---|---|
| 5,432,543 A * | 7/1995 | Hasegawa et al. ............... 348/45 |
| 5,956,416 A | 9/1999 | Tsuruoka et al. |
| 6,026,174 A | 2/2000 | Palcic et al. |
| 6,956,602 B2 * | 10/2005 | Higuchi et al. .................. 348/65 |
| 2007/0191677 A1 * | 8/2007 | Nishimura et al. ........... 600/109 |

FOREIGN PATENT DOCUMENTS

| JP | 2000-155840 | 6/2000 |
|---|---|---|
| JP | WO 02/073507 | 9/2002 |
| JP | 2002-336193 A | 11/2002 |
| JP | 2003-533674 | 11/2003 |
| JP | 2004-261581 | 9/2004 |
| JP | 2004-261582 | 9/2004 |
| JP | 2005-137395 | 6/2005 |
| WO | WO 01/69199 A2 | 9/2001 |

OTHER PUBLICATIONS

Extended Supplementary European Search Report dated Oct. 2, 2009.

* cited by examiner

*Primary Examiner* — Tom Y Lu
(74) *Attorney, Agent, or Firm* — Scully, Scott, Murphy & Presser, P.C.

(57) ABSTRACT

A medical image processing method for image processing of a medical image picking up an image of a living mucous comprises a boundary information detecting step for detecting boundary information corresponding to a boundary portion of a living mucous from the medical image and a mucous feature detecting step for detecting presence of a living mucous with a different feature on the basis of the boundary information detected at the boundary information detecting step.

15 Claims, 27 Drawing Sheets

EXTRACTED EDGE $P_{5x} = (P_{1x} + P_{2x} + \cdots + P_{9x})/9$ $P_{5y} = (P_{1y} + P_{2y} + \cdots + P_{9y})/9$

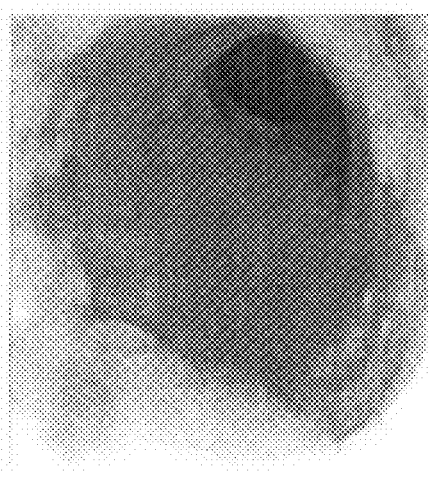
FIG.13A
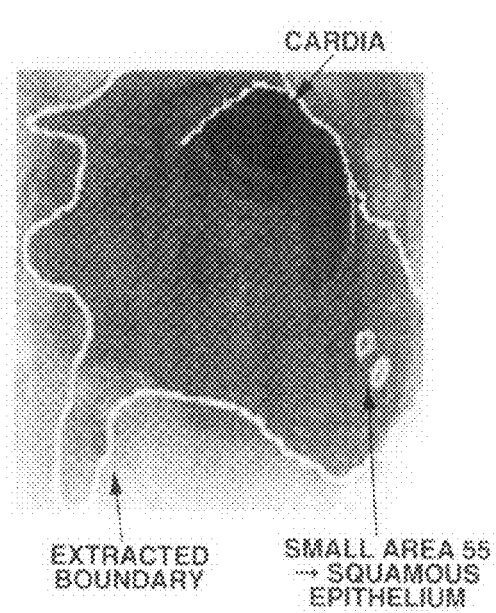
FIG.13B
FIG.14
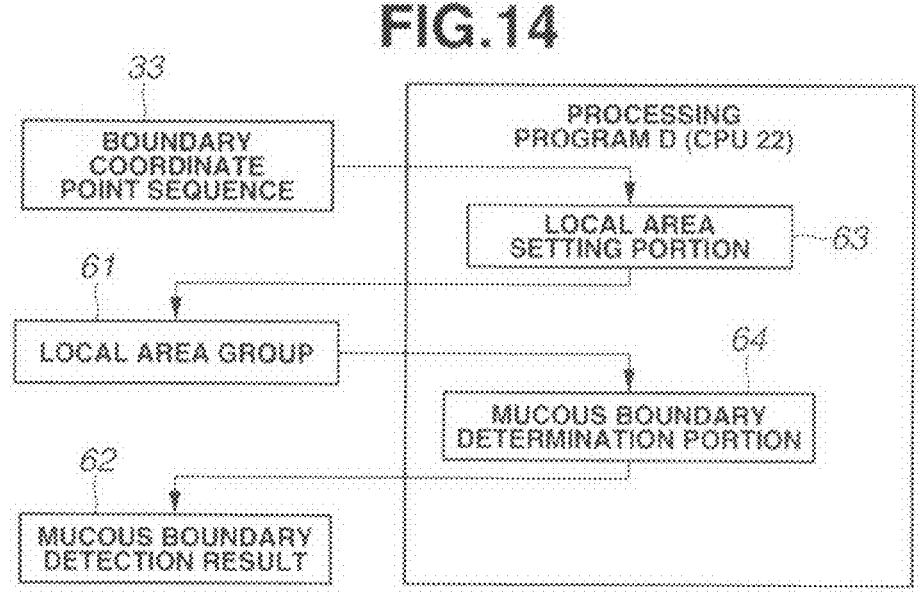

MEDICAL IMAGE PROCESSING METHOD

CROSS REFERENCE TO RELATED APPLICATION

This application is a continuation application of PCT/JP2005/022562 filed on Dec. 8, 2005 and claims the benefit of Japanese Applications No. 2004-359054 filed in Japan on Dec. 10, 2004 and No. 2004-360319 filed in Japan on Dec. 13, 2004, the entire contents of each of which are incorporated herein by their reference.

BACKGROUND OF THE INVENTION

1. Field of the Invention

The present invention relates to a medical image processing method which identifies characters of a mucous tissue or the like in the vicinity of a boundary from an esophagus to a gaster.

2. Description of the Related Art

Recently, an endoscope device for carrying out endoscopic inspections using an endoscope has been widely employed in the medical and industrial fields. In the medical field, the endoscope is used by inserting an insertion portion of an endoscope into a body cavity so as to observe a portion to be inspected and to diagnose if the inspected portion is in the normal state or in the feature-changed state where its feature has changed.

In this case, if determination on whether the state is normal or feature-changed can be made by image processing from an endoscopic image, an operator can make an efficient diagnosis by diagnosing the portion of the determination result with an emphasis.

Japanese Unexamined Patent Application Publication No. 2000-155840, for example, describes a conventional example that a feature value is calculated on the basis of information relating to the shape of a boundary between a feature-changed portion and a normal portion by reducing an influence of an image pickup condition.

A Barrett's mucous is a squamous epithelium of an esophagus replaced by a gastric mucous at a joint portion between the esophagus and the gaster (mucous boundary) due to an influence of gastroesophageal reflux disease or the like. If the Barrett's mucous is generated for 3 cm or more from the normal mucous boundary on the whole circumference of an esophagus luminal section, it is diagnosed as Barrett esophagus disease.

The Barrett esophagus is on the increase particularly in the United States and Europe and causes a serious problem since glandular cancer might be caused with a high probability, and thus, early detection of the Barrett's mucous is extremely important.

The Barrett's mucous progresses not only in the case of occurrence on the whole circumference of the esophagus but often locally and causes a mucous boundary image in a tongue state or zigzag state (referred to as a Z line in some cases).

The Barrett's mucous can be diagnosed in some cases even if the squamous epithelium of the esophagus remains isolated in an island state in the Barrett's mucous and no boundary in the tongue state or the like can be found. Also, the squamous epithelium of the esophagus presents a white tone, while the Barrett's mucous presents a red tone.

SUMMARY OF THE INVENTION

A medical image processing method for image processing of a medical image picking up an image of a living mucous in a first aspect of the present invention comprises:

a boundary information detecting step for detecting boundary information corresponding to a boundary portion of the living mucous from the medical image; and a mucous feature detecting step for detecting presence of a living mucous with a different feature on the basis of the boundary information detected at the boundary information detecting step.

Also, a medical image processing method for image processing of an image signal corresponding to a medical image in two or more colors picking up an image of a living mucous in a second aspect of the present invention comprises:

a first step for setting a processing target area by excluding an inappropriate pixel from a detection target in the medical image;

a second step for calculation processing of a tone feature value for one or more pixels at least in the processing target area; and a third step for detection processing of presence of a specific living mucous on the basis of the calculated tone feature value.

BRIEF DESCRIPTION OF THE DRAWINGS

FIG. 13A is a view showing an image example of the original image.

FIG. 13B is a view showing an image in which a boundary coordinate point sequence is set in the original image of FIG. 13A.

FIG. 14 is a bock diagram illustrating a configuration of a processing function to generate a mucous boundary detection result by the CPU according to a processing program in a third embodiment of the present invention.

DETAILED DESCRIPTION OF THE PREFERRED EMBODIMENTS

Hereinafter, embodiments of the present invention will be described with reference to the drawings.

First Embodiment

A first embodiment of the present invention will be described referring to FIGS. 1 to 10.

Figure 1:
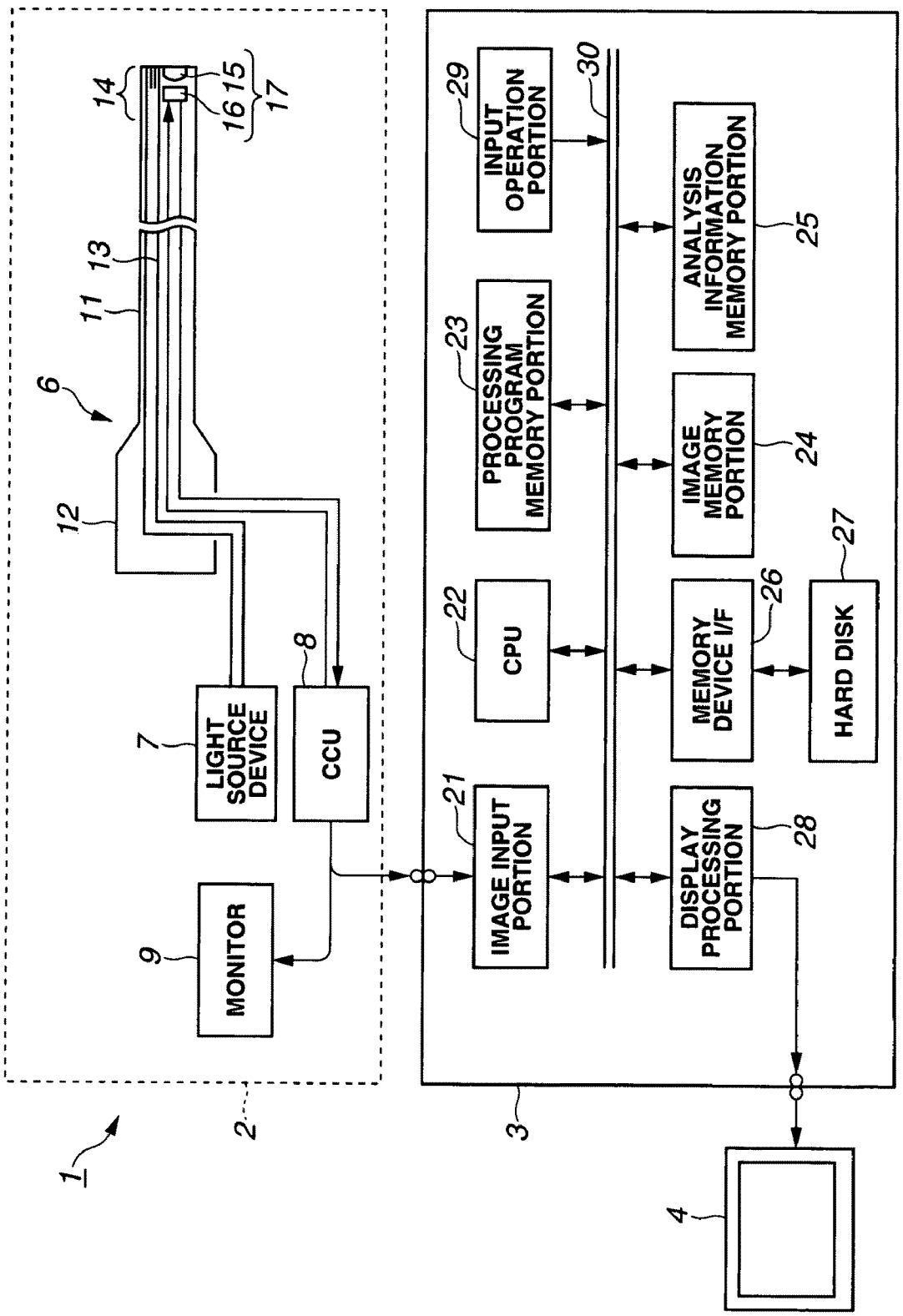
FIG. 1 is a block diagram illustrating a configuration of an endoscope system provided with a function of an image processing method of a first embodiment of the present invention.

An endoscope system 1 shown in FIG. 1 comprises an endoscopic observing device 2, an image processing device 3 comprised by a personal computer or the like for image processing of an image obtained by the endoscopic observing device 2, and a display monitor for displaying an image processed by the image processing device 3.

The endoscopic observing device 2 has an endoscope 6 inserted into a body cavity, a light source device 7 for supplying illumination light to the endoscope 6, a camera control unit (abbreviated as CCU) 8 for signal processing for image pickup means of the endoscope 6, and a monitor 9 for displaying an endoscopic image picked up by an image pickup device when a video signal outputted from the CCU 8 is inputted.

The endoscope 6 has an insertion portion 11 inserted into the body cavity and an operation portion 12 provided at a rear end of the insertion portion 11. A light guide 13 transmitting the illumination light is inserted through the insertion portion 11.

The rear end of the light guide 13 is connected to the light source device 7. And the illumination light supplied from the light source device 7 is transmitted by the light guide 13, and the transmitted illumination light is emitted from a tip-end face attached to an illumination window provided at a tip end portion 14 of the insertion portion 11. A subject such as an affected portion is illuminated by the illumination light.

An objective lens 15 attached to an observation window adjacent to the illumination window and a charge coupled device (abbreviated as CCD) 16, for example, as a solid image pickup device arranged at an image forming position of the objective lens 15 constitute an image pickup device 17. And an optical image formed on an image pickup surface of the CCD 16 is photoelectrically converted by the CCD 16.

The CCD 16 is connected to the CCU 8 via a signal line and the CCD 16 outputs a photoelectrically converted image signal when a CCD driving signal from the CCU 8 is applied. The image signal is processed by a video processing circuit in the CCU 8 and converted to a video signal. The video signal is outputted to the monitor 9, and on the display surface of the monitor 9, an image corresponding to the video signal and picked up by the CCD 16 is displayed as an endoscopic image. The video signal is also inputted to the image processing device 3.

In this embodiment, the endoscope 6 is used in an endoscopic inspection where the tip end portion 14 of the insertion portion 11 is inserted from a mouth portion to a vicinity of a boundary between an esophagus and a gaster to examine whether a Barrett's mucous as a mucous membrane in which a normal mucous membrane of an esophagus (squamous epithelium to be specific) as a mucous membrane to be detected is changed (also referred to as feature-changed mucous in this specification) so as to present the feature of a gastric mucous portion exists or not in the vicinity of the boundary.

In this case, a video signal corresponding to an endoscopic image picking up a living mucous surface in the body is also inputted to the image processing device 3, and detection (determination) processing on whether the Barrett's mucous exists or not is carried out by an image processing method for the video signal as will be described later.

The image processing device 3 has an image input portion 21 to which a video signal corresponding to an endoscopic image inputted from the endoscopic observing device 2 is inputted, a central processing unit (abbreviated as CPU) 22 for image processing of image data inputted from the image input portion 21, and a processing program memory portion 23 storing a processing program (control program) for execution of the image processing by the CPU 22.

The image processing device 3 also has an image memory portion 24 storing image data and the like inputted from the image input portion 21, an analysis information memory portion 25 storing analysis information processed by the CPU 22, a hard disk 27 as a memory device storing the image data and the analysis information processed by the CPU 22 via a memory device interface 26, a display processing portion 28 for display processing for displaying the image data and the like processed by the CPU 22, and an input operation portion 29 comprised by a keyboard and the like with which a user carries out data input of parameters and instruction operation of the image processing.

The video signal created by the display processing portion 28 is outputted to the display monitor 4 and the processed image given image processing is displayed on a display surface of the display monitor 4. The image input portion 21, the CPU 22, the processing program memory portion 23, the image memory portion 24, the analysis information memory portion 25, the memory device interface 26, the display processing portion 28, and the input operation portion 29 are connected to each other via a data bus 30.

Figure 2:
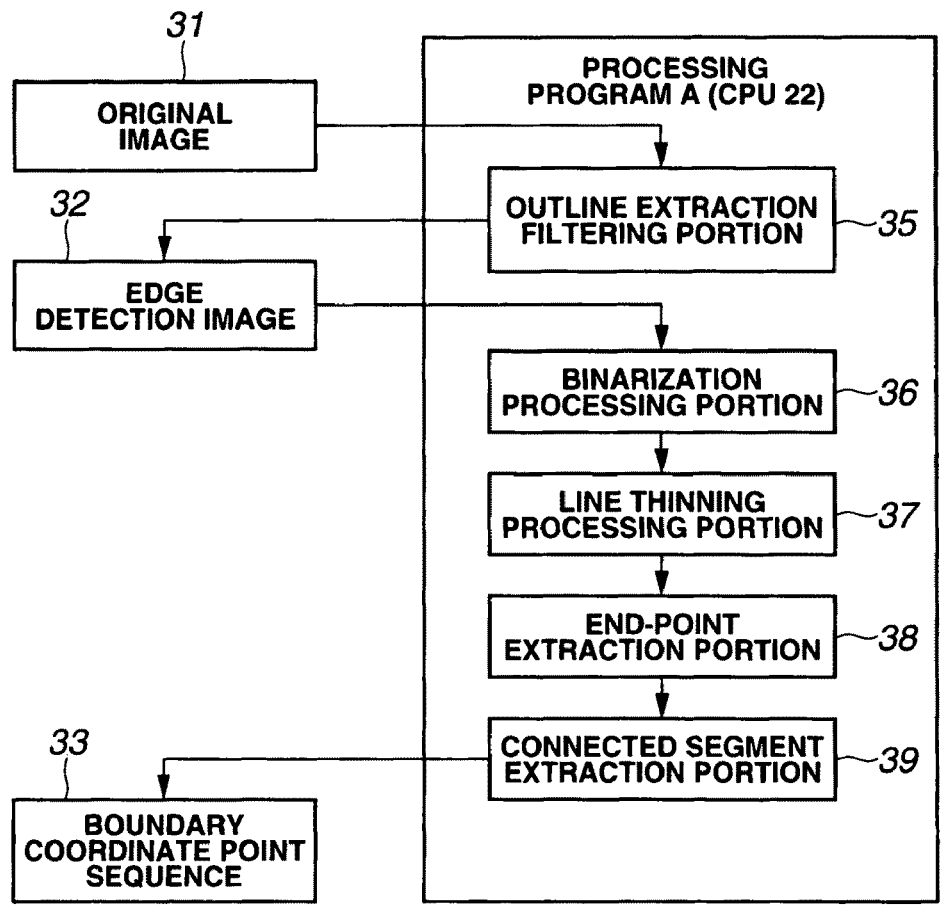
FIG. 2 is a block diagram illustrating a configuration of a processing function to generate a boundary coordinate point sequence by a CPU according to a processing program.
Figure 3:
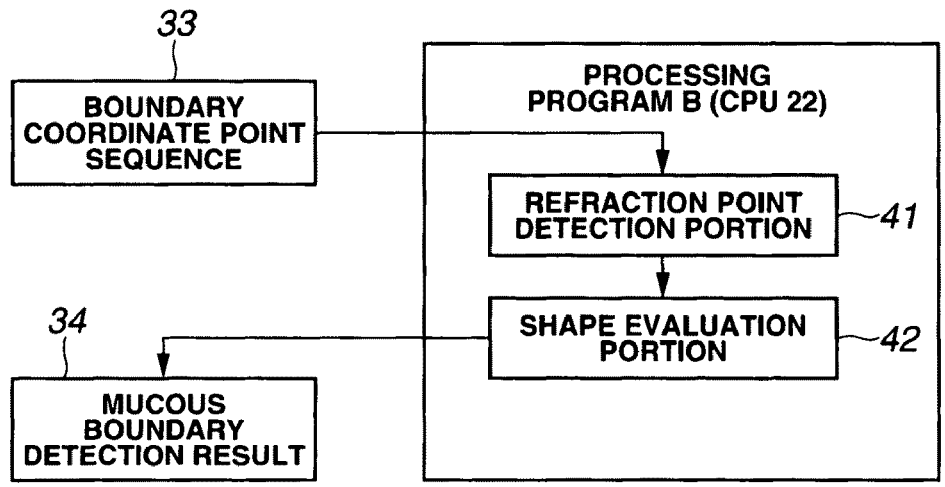
FIG. 3 is a block diagram illustrating a configuration of a processing function to generate a mucous boundary detection result by the CPU according to the processing program.

In the present embodiment, as shown in FIGS. 2 and 3, by the processing of a processing program A and a processing program B stored in the processing program memory portion 23, the CPU 22 executes image processing to detect (determine) the Barrett's mucous as the feature-changed mucous whose feature is different from a normal mucous as a detection target mucous. The processing program A in FIG. 2 creates an edge detection image 32 from an original image 31 and carries out a processing to create a boundary coordinate point sequence 33. And the processing to create a mucous boundary detection result 34 is executed by the processing program B shown in FIG. 3 for the boundary coordinate point sequence 33.

As shown in FIG. 2, the CPU 22 executing the processing program A has a function of an outline extraction filtering portion 35 for generating the edge detection image 32 by carrying out outline extraction filtering for the original image 31. That is, concentration values in R, G, B of image data are different between a normal mucous and a feature-changed mucous. Therefore, by detecting or extracting an edge, a boundary between the normal mucous and the feature-changed mucous can be detected. The concentration values of RGB of the image data are made into values given known reverse γ correction.

The outline extraction filtering portion 35 generates the edge detection image 32 by application of a known band-pass filter or a known edge detection filter (Prewitt operator, Sobel operator, for example). The detail of the edge detection filter can be found in Document 1: "Introduction to Computer Graphics by Hideyuki Tamura, Soken Shuppan, pp. 120 to 122".

The CPU 22 for executing the processing program A has a binarization processing portion 36 for binarization processing for the edge detection image 32, a line thinning processing portion 37 for line thinning processing after the binarization processing, an end-point extraction portion 38 for extracting an end point after the line thinning processing, and a connected segment extraction portion 39 for generating the boundary coordinate point sequence 33 by connected segment extraction after the end-point extraction.

The binary processing portion 36 sets a predetermined threshold value θ for the edge detection image 32 and generates a binary image by setting a pixel not smaller than the threshold value θ to 1 and a pixel smaller than the predetermined threshold value to 0.

The line thinning processing portion 37 generates a line-thinned image with a pixel value of the line at 1 and a pixel value of the background at 0 for the binarized image. The line thinning processing portion 37 can use a method known as the Hildlich line thinning method and carries out processing to reduce the line width with the pixel value of the pixel as 0 when connectivity of the pixels can be held.

For the Hildlich line thinning method, see Document 2: "C MAGAZINE 2000, September, published by Softbank, "Algorithm Lab for Ultimate Image processing" pp. 123 to 129".

The end-point extraction portion 38 sequentially obtains data in a 3×3 pattern along the scanning direction of a screen for an image given the line thinning processing by the line thinning processing portion 37. When the pixel value at the center of the obtained pattern is "1" and there is only one pixel with the pixel value="1" in the upper, lower, right and left sides around, the pixel at the center point is determined as an end point, in other words, as a boundary point.

The connected segment extraction portion 39 acquires a boundary coordinate point sequence by carrying out trace processing for the line-thinned image with one end-point (boundary point) as a starting point.

The trace processing is achieved by a known boundary line tracing processing and is detailed in Document 3: "Introduction to Computer Graphics by Hideyuki Tamura, Soken Shuppan, pp. 84 to 85".

The CPU 22 executing the processing program A shown in FIG. 3 has functions of a refraction point detection portion 41 for detecting a refraction point (bent point) for the boundary coordinate point sequence 33 and a shape evaluation portion 42 generating the mucous boundary detection result 34 by shape evaluation of the boundary coordinate point sequence 33 in which the refraction point is detected.

When the refraction point satisfying the condition is detected, as will be described later, the shape evaluation portion 42 determines the point as a feature-changed mucous boundary if the number of refraction points is not less than a predetermined value and determines the point as not a feature-changed mucous boundary when there is no irregularity of refraction (bending), that is, there is only one direction of the refraction satisfying the condition.

Next, an image processing method for Barrett's boundary determination on a specific mucous to be determined or specifically, a Barrett's mucous boundary or not (as a feature-changed mucous in which a squamous epithelium as a normal mucous of an esophagus has changed) by the processing programs A and B in FIGS. 2 and 3 will be described by a processing flow in FIG. 4.

When the operation of the image processing device 3 is started, the CPU 22 reads the processing program in the processing program memory portion 23 and starts the processing according to the processing program. That is, the function of the processing program A shown in FIG. 2 is performed. More specifically, as shown in FIG. 4, the CPU 22 obtains, at the first Step S1, image data as the original image 31 inputted from the CCU 8 of the endoscope observing device 2 via the image input portion 21.

Figure 5A:
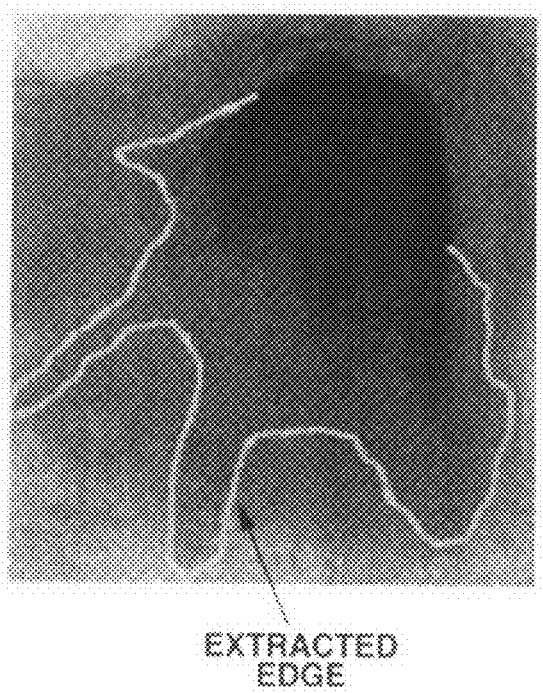
FIG. 5A is a view showing an image example in which an edge extracted from an original image is set.

Then, at the subsequent Step S2, the CPU 22 carries out the above-mentioned known edge detection processing as the edge extraction filtering processing so as to generate the edge detection image 32. FIG. 5A shows the edge detection image 32. In an image picking up the inside of the luminal esophagus obtained by a direct view type endoscope 6 shown in FIG. 1, the deep portion of the lumen (gastric side) becomes a dark part. The dark part in an image in FIG. 5A corresponds to the vicinity of a cardia close to an entrance of a gaster.

At the subsequent Step S3, the CPU 22 carries out the above-mentioned binarization processing for the edge detection image 32 and moreover, executes the line thinning processing and end-point extraction (obtainment of a boundary).

At the subsequent Step S4, the CPU 22 carries out the trace processing for the obtained boundary so as to obtain a coordinate point sequence along the boundary, that is, a coordinate point sequence of the boundary.

Then, the CPU 22 carries out the processing of the processing program B in FIG. 3. That is, for the coordinate point sequence of the boundary generated at Step S4, the CPU 22 calculates N pieces of bent refraction points, for example, on the basis of a vertex evaluation value A of each point on the boundary as shown in Step S5.

Figure 6:
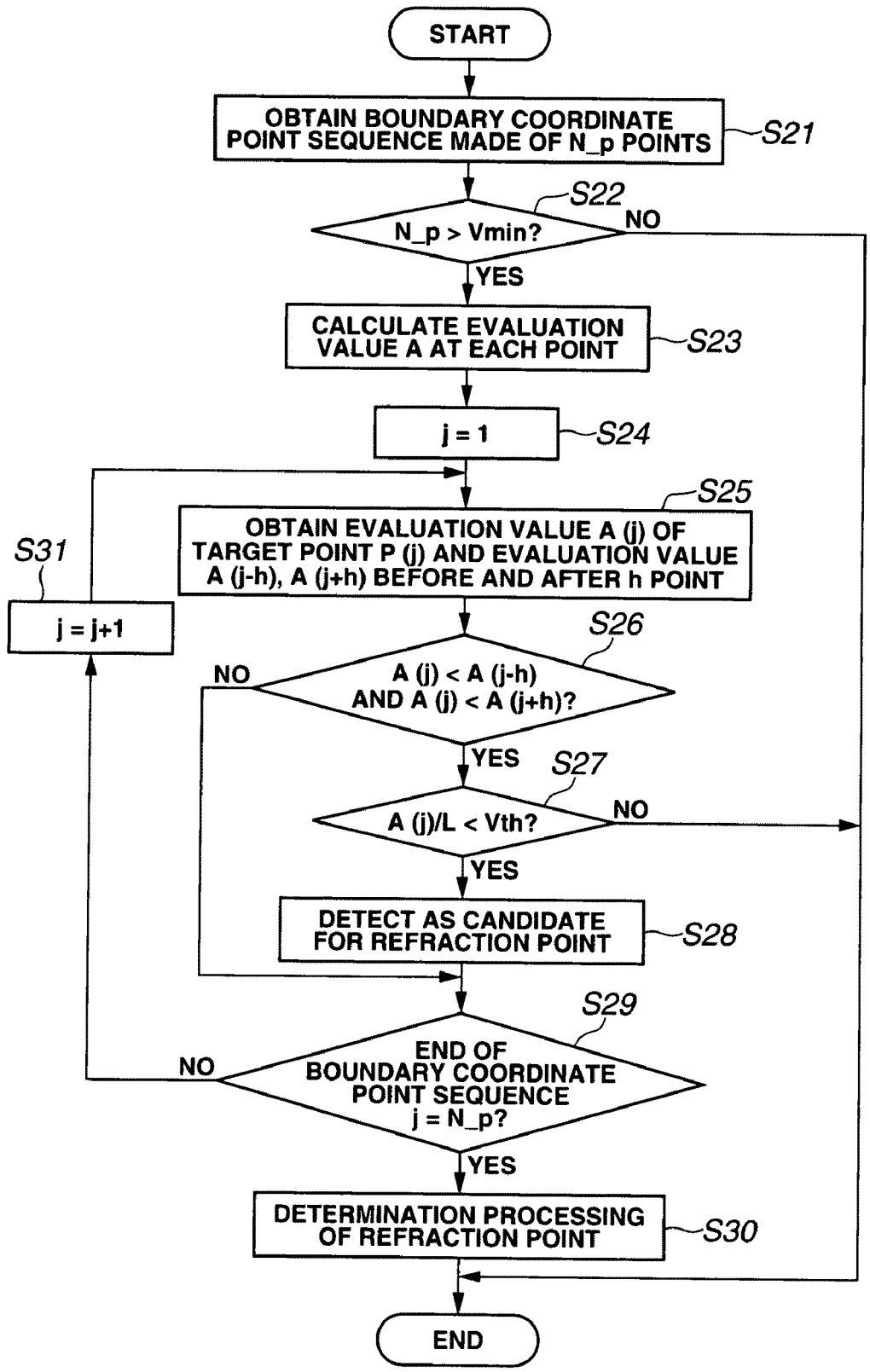
FIG. 6 is a flowchart illustrating a processing procedure to determine a refraction point from the boundary coordinate point sequence.

The calculation processing of the refraction point will be described later using FIG. 6, but when described in brief using FIG. 7, a curve with the length of L/2 is extracted (set) before and after each point as the center on the boundary, a straight distance (chord length) between the start point and the end point is calculated as a vertex evaluation value A(j), and those smaller than the vertex evaluation value A(j−h) and A(j+h) before and after by h point are made as candidates for the refraction point, and a refraction point is determined from the candidates.

At the subsequent Step S6, the CPU 22 initializes a parameter k indicating the number of control points and a parameter i of the refraction point to 0, 1, respectively, and starts processing to determine presence of the feature-changed mucous to be detected.

After the parameters i, k are initialized, at the subsequent Step S7, the CPU 22 determines if an evaluation value B is smaller than a predetermined threshold value thr or not in the calculated refraction point (i). In this case, the CPU 22 calculates a vertex evaluation value A/L as the evaluation value B and determines if the evaluation value B in the refraction point (i) is smaller than the predetermined threshold value thr or not.

The CPU 22 compares the evaluation value B calculated in the refraction value (i) with a reference value thr set to identify sample data sampled from the normal mucous and the feature-changed mucous whose feature has changed, or more specifically, each of the squamous epithelium and Barrett's mucous determined in advance by diagnosis.

When the condition of the evaluation value B<thr is satisfied, at Step S8, the CPU 22 obtains the refraction point (i) as a control point M and increments the value of the parameter k by one. On the other hand, if the condition of the evaluation value B<thr is not satisfied, the routine goes to Step S9.

At Step S9, the CPU 22 determines if the processing of Steps S7 and S8 has been executed for all the refraction points by determination on whether the parameter i is the final refraction point, that is, if i is N or not. If the processing has not been completed for all the refraction points, the parameter i is incremented by one as shown in Step S10, and the routine returns to Step S6.

Figure 5B:
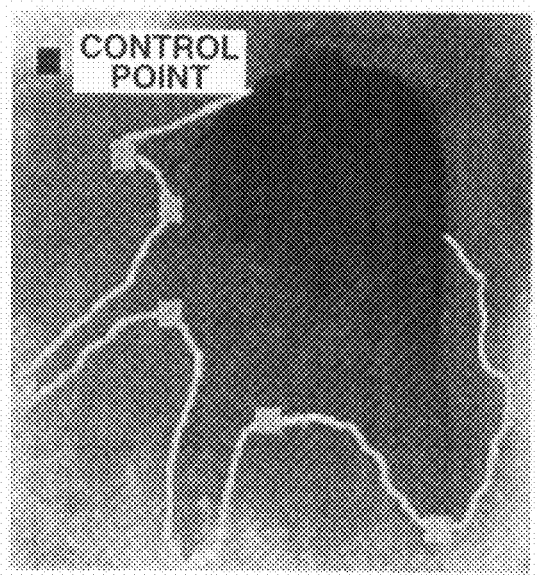
FIG. 5B is a view showing an image example in which a control point for determination of the shape from the original image is set.

When the CPU 22 executes the processing of Steps S7 and S8 for all the refraction points as above, a control point is set as shown in FIG. 5B and the routine goes on to Step S11.

At Step S11, the CPU 22 determines if the parameter k of the number of control points is larger than 1 or not. If the parameter k is determined to be larger than 1, the CPU 22 determines at the subsequent Step S12 whether the arrangement of the control points are irregular in the radial direction of the lumen.

If the control points are not in the concentric state but arranged in the irregular shape in the radial direction of the lumen as shown in FIG. 5B, the CPU 22 determines the case as a boundary of the Barrett's mucous, that is, the Barrett's boundary as shown in FIG. 13.

On the other hand, if the condition of k>1 is not satisfied at the determination at Step S11, and if the arrangement of the control points is not irregular in the radial direction but in the concentric state at the determination of Step S12, the CPU 22 makes determination as a boundary of a squamous epithelium as a normal mucous, as shown in Step S14. In this way, a possibility of presence of a boundary of the Barrett's mucous (Barrett's boundary) in the image can be determined from the image data.

Next, processing of refraction point calculation at the boundary in Step S5 will be described referring to FIG. 6.

At Step S21, the CPU 22 obtains the boundary coordinate point sequence made of N_p pieces of points.

At Step S22, the CPU 22 makes comparison the sequence with a threshold value Vmin of the minimum number of points of the boundary coordinate point sequence to be processed. In the case of N_p>Vmin, the routine goes on to Step S23, while if not, the routine is finished as not applicable for the processing.

At the subsequent Step S23, the CPU 22 calculates the vertex evaluation value A(j) (1≦j≦N_p) of the refraction point at each point. The detail of step S23 will be described later.

At the subsequent Step S24, j is initialized, and at Step S25, the CPU 22 makes the point P(j) as a target point and obtains a vertex evaluation value A(j) of the refraction point at the target point and the vertex evaluation value A(j−h), A(j+h) of the refraction point at points P(j−h), P(j+h) before and after the target point by h points. The value h is a parameter for selecting a comparison target at Step S26, and in the present embodiment, it is h=5, for example. The detail of the Step S25 will be described later.

At Step S26, the CPU 22 compares the vertex evaluation value A(j), A(j−h), A(j+h) of the refraction point. In the case of A(j)<A(j−h) and A(j)<A(j+h), the routine goes onto Step S27, while if not, the routine goes on to Step S29. The detail of Step S26 will be described later.

At Step 27, the CPU 22 makes comparison with a threshold value Vc for limiting the size of refraction for refraction detection. In the case of A(j)/L<Vc, the routine goes on to Step S28, while if not, the processing is finished.

At Step S28, the CPU 22 detects the target point P(j) as a candidate point of the refraction point and stores the information in the analysis information memory portion 25 and the like.

At Step S29, if the target point P(j) is the final point of the boundary coordinate point sequence, that is, j=N_p, the CPU 22 determines the refraction point at Step S30 and finishes the processing, while in the case of j≠N_p, the routine goes on to Step S31.

At Step S31, the CPU 22 updates the target point as j=j+1, and a series of processing shown in Steps S25 to S29 is repeated.

Figure 9:
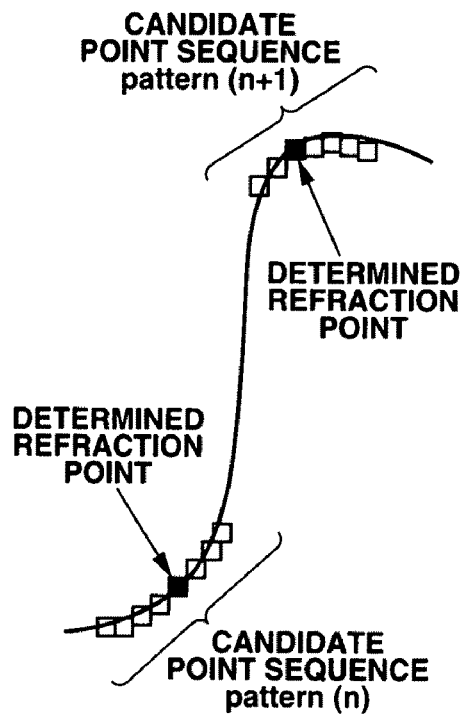
FIG. 9 is an explanatory view for determination of the refraction point from a candidate point sequence of the refraction point.

A flow of refraction point determination processing at Step S30 is shown in FIG. 9, and the detail will be described later.

Next, a calculation method of the vertex evaluation value A of the refraction point at Step S23 and detection processing of a candidate point of the refraction point using the vertex evaluation value A of the refraction point at Step S25, Step S26 will be described.

Figure 7:
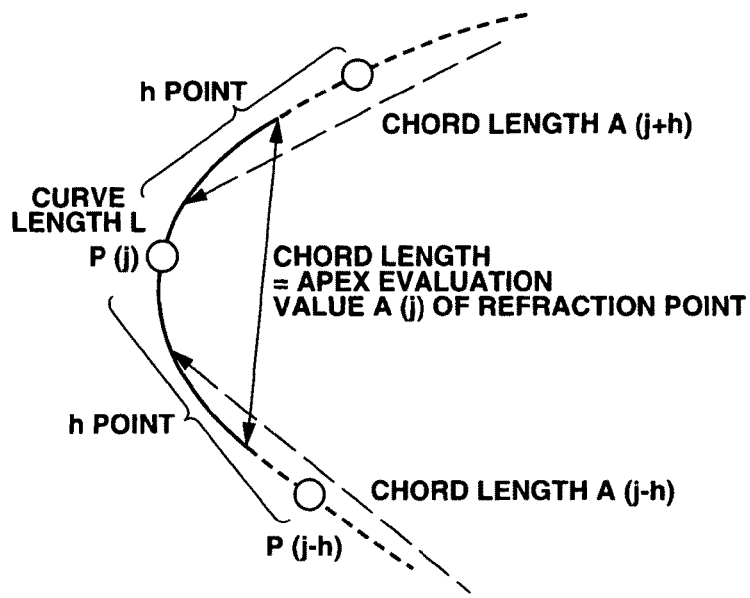
FIG. 7 is an explanatory diagram for calculation of a vertex evaluation value of the refraction point in the processing procedure in FIG. 6.

FIG. 7 is an explanatory view for explaining the calculation method of the vertex evaluation value A of the refraction point and the detection processing of the candidate point of the refraction point using the vertex evaluation value A of the refraction point in the present embodiment.

For the calculating method of the vertex evaluation value A of the refraction value, a method shown in Document 4: "'Method of Detecting Refraction Point of Line-thinned Figure' by Koyama et al., material for Electronic Communication Society Study Group, PRL80-107, pp. 80 to 90 (1980)" is used.

The CPU extracts a curve with the length L shown by a solid line in FIG. 7 with each point at the center for each point of the obtained boundary coordinate point sequence along the point sequence and calculates a distance between the start point and the end point (chord length) of the curve as the vertex evaluation value A(j) of the refraction point. However, if the point P(j) exists in a range of [L/2] from both ends of the boundary coordinate point sequence and the curve with the length L can not be extracted, it is set as A(j)=L. Here, [ ] is a gauss symbol.

Also, if the point P(j) exists in a range of h from the both ends in the detection processing of a candidate point of the refraction point and the point P(j−h), P(j+h) can not exist at a point on the boundary coordinate point sequence, it is set as A(j−h)=L, A(j+h)=L. If the vertex evaluation value A(j) of the refraction point at the point P(j) is smaller than the vertex evaluation value A(j−h) at the point P(j−h) before by the h point and the vertex evaluation value A(j+h) of the refraction point at the point P(j+h) after by the h point, P(j) shows a feature of refraction larger than the point P(j−h), P(j+h), and the CPU 22 detects P(j) as a candidate point of the refraction point.

The comparison evaluation is made sequentially for all the points forming the boundary coordinate point sequence. The range of [L/2] from the both ends of the boundary coordinate point sequence, where A(j)=L as mentioned above, is excluded from detection of a candidate point of the refraction point.

Figure 8:
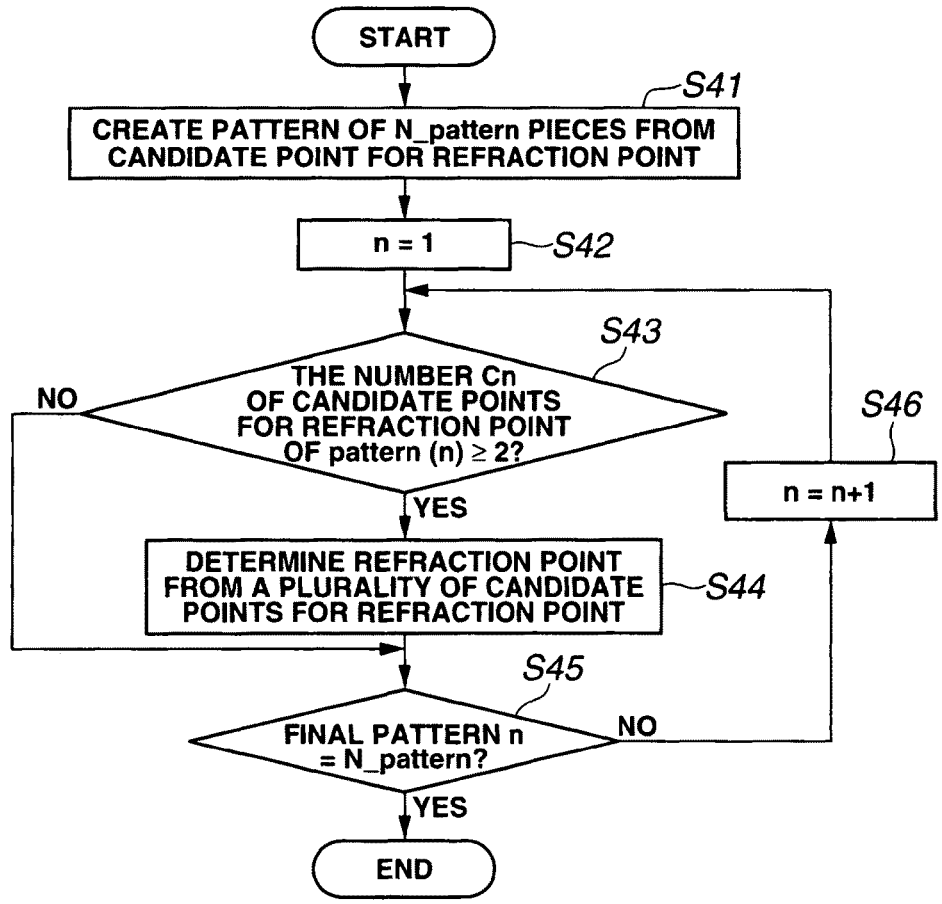
FIG. 8 is a flowchart illustrating a processing procedure to determine the refraction point from a candidate point for the refraction point.

Next, a processing flow in the determination processing of the refraction point is shown in FIG. 8.

At Step S41, the CPU 22 obtains a candidate point of the refraction point detected by the above-mentioned detection processing of a candidate point of the refraction point from the analysis information memory portion 25. If the candidates points of the refraction point continue adjacently, the point sequence is extracted as a set (hereinafter referred to as pattern). The number of patterns generated in the boundary coordinate point sequence is set as N_pattern (1≦N_pattern≦the number of candidate points of the refraction point), and the CPU calculates the number of candidate points Cn (1≦n≦N_pattern) of the refraction points forming each pattern.

At Step S42, the CPU 22 executes initialization to n=1 indicating the first pattern and at Step S43, the CPU 22 obtains one of the patterns generated at Step S41 as the target point pattern(n) (1≦n≦N_pattern).

In the case of the number of candidates of the refraction point Cn=1 of the target pattern pattern(n), the CPU 22 determines that the other candidates of the refraction points are not adjoined but exist independently and determines the refraction point as a candidate of the refraction point.

In the case of the number of candidates of the refraction point Cn≧2 of the target pattern pattern(n), the routine goes on to Step S44, and the CPU 22 determines one point from the candidate point sequence of the refraction point of the target pattern as the refraction point.

At Step S44, the CPU 22 determines a point with the minimum A(j) as the refraction point in the target pattern pattern(n). FIG. 9 is a view illustrating determination of a refraction point from candidate points of the refraction point.

At Step S45, if the target pattern pattern(n) is the final pattern, that is, n=N_pattern, the CPU 22 finishes the processing, while in the case of n≠N_pattern, the routine goes on to Step S46.

At Step S46, the CPU 22 updates the target pattern of refraction-point determination as n=n+1, and a series of processing shown in Steps S43 to S45 is repeated.

If the boundary coordinate point sequence is not smooth, in the boundary coordinate point sequence obtained at Step S21, the coordinate values are smoothed by a moving average method as shown in the above Document 4.

Figure 10:
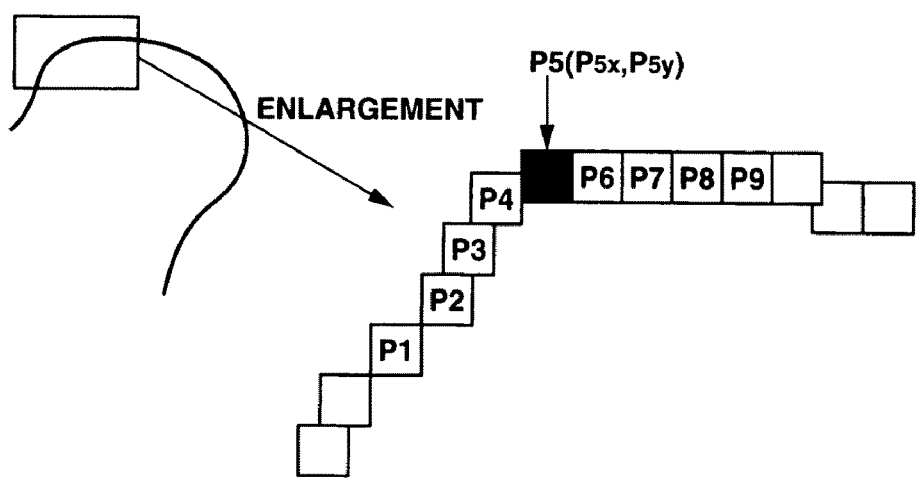
FIG. 10 is an explanatory view for smoothing of the boundary coordinate point sequence by moving average.

The moving average method herein is a method for setting the coordinate value of the point P to an average value of the coordinate value of front and rear [m/2] points of the coordinate point sequence. The value m is a parameter determining the number of moving average points, that is, the intensity of smoothing. For example, a case using m=9 as shown in FIG. 10, that is, the moving average of 9 points is illustrated.

Since A(j)=L is supposed in a range of [L/2] from the both ends of the boundary coordinate point sequence, a candidate point of the refraction point is not detected, but if it is to be included in the detection target, as shown in the above patent document, the both ends of the boundary coordinate point sequence obtained at Step S21 may be extended. Alternatively, a parameter h at Step S25 may be determined based on the number of points N_p forming the boundary coordinate point sequence.

In the present embodiment, at Step S44, the CPU 22 determines the point where A(j) of the candidate point sequence of the refraction point in the target pattern becomes the minimum as the refraction point, but a center point in the candidate point sequence of the refraction point in the target pattern, that is, the [Cn/2]-th point may be determined.

As mentioned above, in the present embodiment, a mucous boundary with different feature is detected by edge detection processing or the like for the original image 31, a refraction point in the shape of the mucous boundary is detected, and depending on whether the refraction point satisfies a predetermined condition or not, the point is set as a control point as a representative point of the refraction point. And on the basis of the control point, whether it is the Barrett's boundary as a boundary of the feature-changed mucous is detected (determined).

In a case where the Barrett's mucous exists in the vicinity of the boundary between an esophagus and a gaster, if the Barrett's mucous exists, the Barrett's mucous boundary appears not in the concentric state but in the irregular shape as a star as shown in FIG. 5B.

Therefore, when a control point as a representative point of the refraction point is detected and the control point is irregularly arranged or the number of control points is more than a predetermined number as above, it is determined as the Barrett's mucous boundary. Thus, the Barrett's mucous can be determined with accuracy according to the feature often found in the case of the Barrett's mucous.

When the Barrett's boundary is to be determined, the determination may be made on whether the boundary is the Barrett's mucous or not based on complicity of the detected boundary. That is, processing for detecting or evaluating that the shape of the detected boundary is not a simple shape such as a circle but has a complicated shape is executed and the determination on the Barrett's boundary may be made based on the evaluation result.

More specifically, a radius of curvature is acquired in the vicinity of points set with a predetermined interval along the boundary coordinate point sequence 33, for example, the values of the radius of curvature are grouped and correspondence whether it is a complicated shape or not is made by distribution of the values of the radius of curvature. And when the distribution of the radius of curvature is not less than a threshold value, the boundary may be determined as the Barrett's mucous boundary.

Second Embodiment

Figure 11:
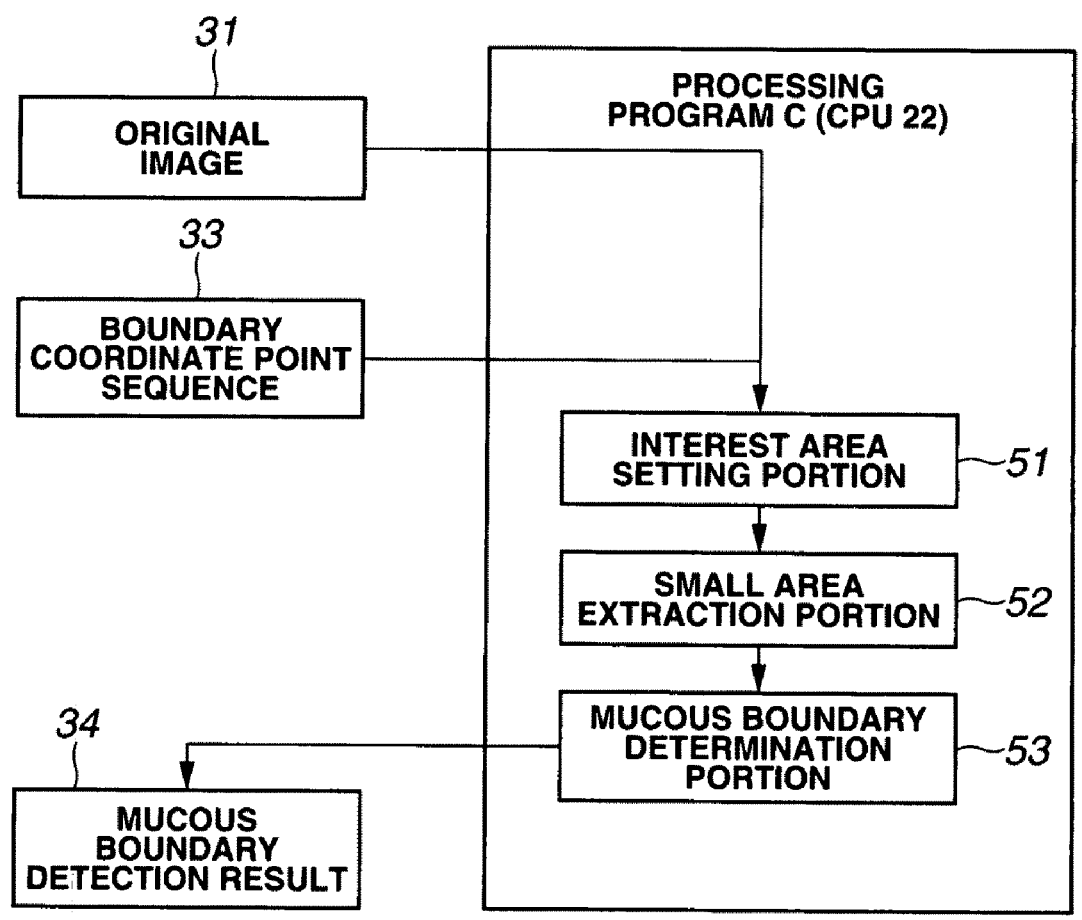
FIG. 11 is a block diagram illustrating a configuration of a processing function to generate a mucous boundary detection result by the CPU according to a processing program in a second embodiment of the present invention.

A second embodiment of the present invention will be described below referring to FIGS. 11 to 13. FIG. 11 shows a functional configuration realized by the CPU 22 according to a program C in the second embodiment.

In the present embodiment, since the portion in FIG. 2 in the first embodiment is the same, the description is omitted, and a processing function shown in FIG. 11, that is, an interest area setting portion 51, a small area extraction portion 52 and a mucous boundary determination portion 53 are provided instead of the processing function in FIG. 3.

As shown in FIG. 11, an interest area to be detected is set by the interest area setting portion 51 for the original image 31 and the boundary coordinate point sequence 33.

For the set interest area, the small area extraction portion 52 extracts a small area, and the mucous boundary determination portion 53 determines if the extracted small area is a mucous boundary or not and outputs a mucous boundary detection result 34.

Then, specific processing will be described referring to a processing flow in FIG. 12.

Figure 4:
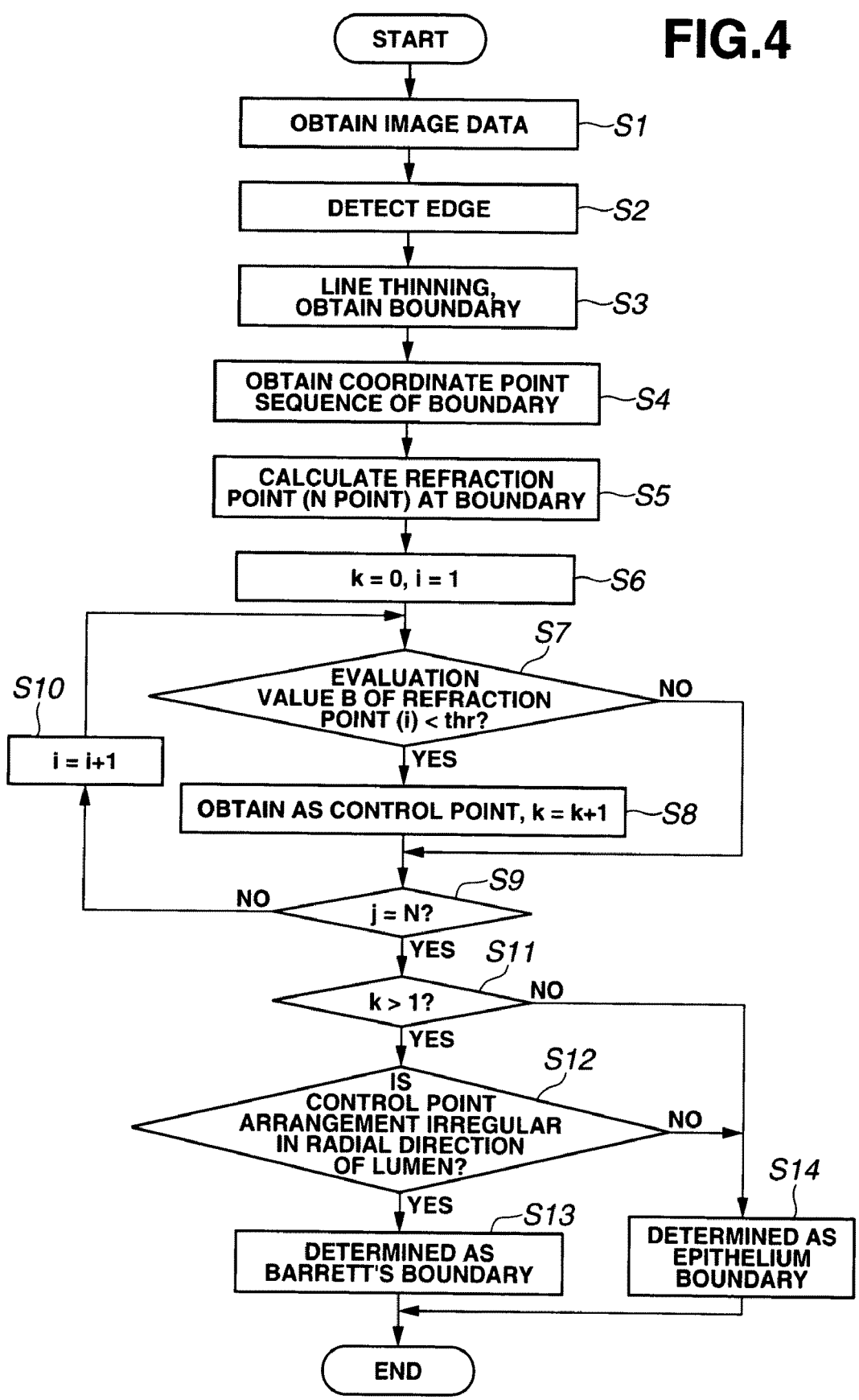
FIG. 4 is a flowchart illustrating a processing procedure processed by the CPU.

Similarly to the case shown in FIG. 4, the CPU 22 obtains image data (S1), detects an edge (S2), generates the edge detection image 32, applies line thinning and obtains a boundary (S3), and moreover, obtains a boundary coordinate point sequence and generates the boundary coordinate point sequence 33 (S4). The following processing may be carried out in the state before generation of the boundary coordinate point sequence 33 (that is, after the processing of Step S3).

At the subsequent Step S51, the CPU 22 sets an area close to a cardia to be on the luminal center side in the image (since the luminal center side becomes dark, extraction is possible in the determination processing using a threshold value of the dark part) or an area including the cardia as the interest area for the area divided by the boundary in Step S4 (S3).

After the interest area is set in this way, as shown in Step S52, the CPU 22 detects an edge in the interest area using the edge detection processing or BPF (band-pass filter) again for the interest area so as to generate an image including a small area 55 divided by the edge as in FIG. 13B from the original image of FIG. 13A.

At the subsequent Step S53, the CPU 22 initializes the parameter i indicating the small area 55 (set to i=1) and then, at the subsequent Step S54, calculates an average tone C(i) in each small area (i).

The average tone C(i) is an average value of the value of IHb, for example. The IHb extracts a brightness signal Vg (color signal of G reflecting light near 560 nm which is absorbed by hemoglobin the most) and a brightness signal Vr (color signal of R reflecting light near 650 nm which is absorbed by hemoglobin the most) for each pixel on an endoscopic image and uses a value obtained by logarithm conversion of a ratio between the two R, G color signals, $32 \log_2 (R/G)$.

And at the subsequent Step S55, the CPU 22 determines if the average tone C(i) is larger than a predetermined threshold value thr2 or not. In this case, the predetermined threshold value is set using an average value of a tone in at least one or more color signals in an image picking up a portion of the Barrett's mucous of a case where a diagnosis is finalized and an average value of a tone in the same color signal in an image picking up a portion of a squamous epithelium.

If the determination result at Step S55 satisfies a determination condition of the average tone C(i)>thr2, as shown in Step S56, the small area (i) is considered to be a squamous epithelium remaining on the Barrett's mucous and if one or more squamous epithelia exists, the CPU 22 determines the interest area including the small area as the Barrett's boundary (Barrett's mucous boundary).

On the other hand, if the determination result at Step S55 does not satisfy the determination condition of the average tone C(i)>thr2, as shown in Step S57, the CPU 22 determines if the parameter i is equal to the number N of the small areas or not, and if it is not equal, i is incremented by 1 as shown in Step S58 and the routine returns to Step S54. And the processing from Step S54 to Step S57 is repeated.

In the case of the Barrett's mucous, the small areas of the squamous epithelia might exist alone in an island state in the Barrett's mucous in many cases.

Thus, in the present embodiment, the boundary coordinate point sequence 33 is generated, an edge or a small area (i) is detected by the boundary coordinate point sequence 33 in the area on the lumen side by the boundary coordinate point sequence 33 in the original image 31, and determination is made on whether each small area (i) is a squamous epithelium or not from the feature value of the tone. If the small area (i) is determined as the squamous epithelium, the squamous epithelium in which a small area is isolated in an island state is determined as the Barrett's mucous or the Barrett's boundary.

As above, determination on whether the Barrett's mucous exists or not in the original image can be made with accuracy.

Figure 12:
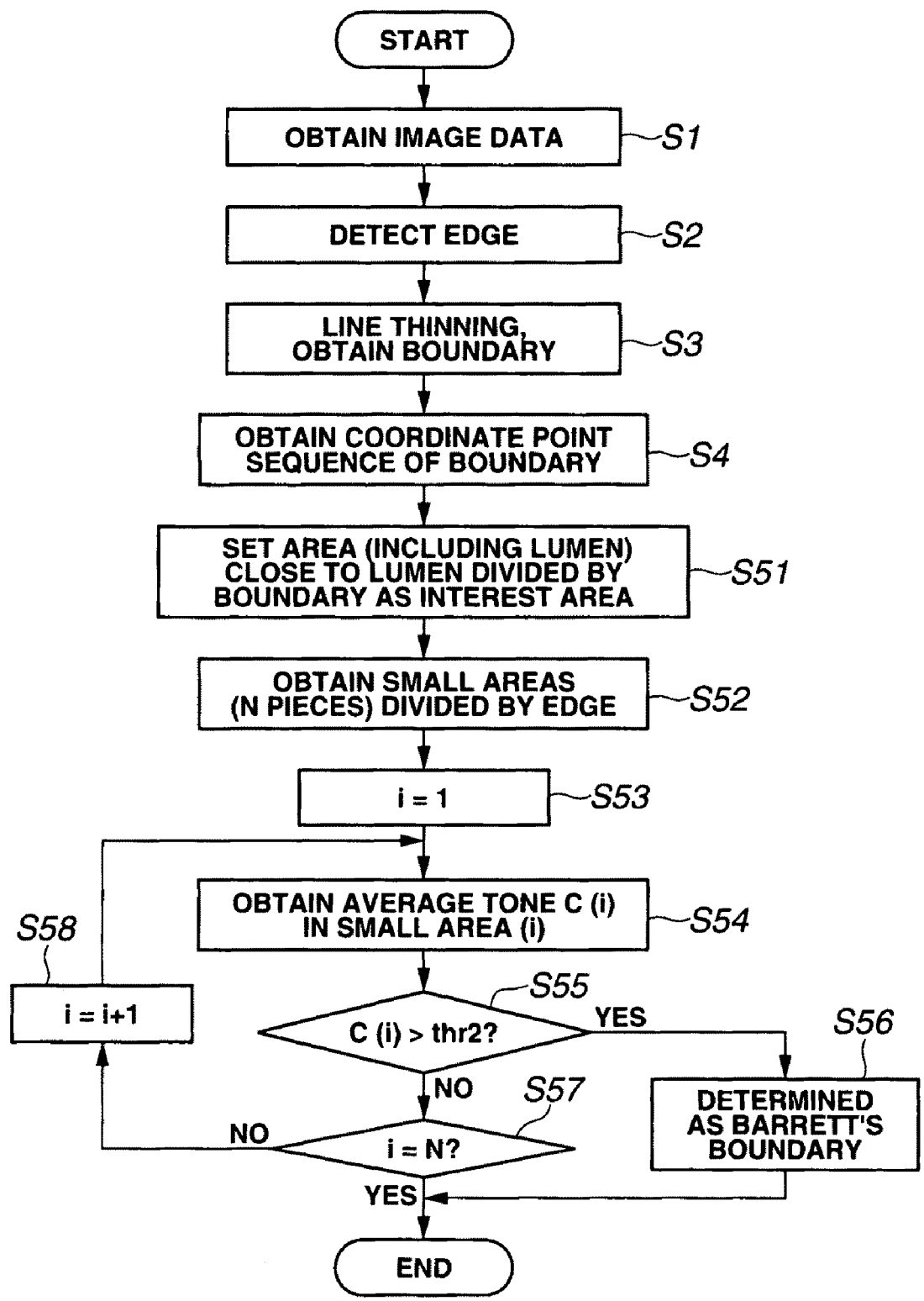
FIG. 12 is a flowchart illustrating a processing procedure processed by the CPU.

At Step S52 in FIG. 12, the small area 55 divided by the edge is detected, but as a variation, the small area 55 may be obtained by binarization with a predetermined threshold value.

Also, at Steps S54, S55, determination on the Barrett's mucous or Barrett's boundary may be made on the basis of a tone change in the front and rear (or both) of the edge in the small area 55.

In the image processing in FIG. 12, the area on the luminal side is set to an interest area and determination is made for the small area 55 divided by the edge or the like in the interest area, but determination may be made by obtaining an average tone for the area outside the small area 55.

For example, comprehensive determination may be made for the interest area on the basis of the determination result of the small area 55 and the determination result of the area outside the small area. Then, more accurate determination can be made.

As the small area 55 divided by the edge, the small area might be completely isolated as shown in FIG. 13B. Also, the small area 55 might be in the shape extended outward and connected to the squamous epithelium.

In this case, since the small area 55 often appears as an isolated curve as shown in FIG. 13B, determination on whether the interest area is the Barrett's mucous or Barrett's boundary may be made on the basis of whether the detected small area 55 is an isolated curve or not.

Third Embodiment

Next, a third embodiment of the present invention will be described referring to FIGS. 14 to 18. FIG. 14 shows a functional configuration realized by the CPU 22 according to a program D in the third embodiment.

The present embodiment has a processing function shown in FIG. 2 in the first embodiment and also has a processing function shown in FIG. 14 instead of the processing function in FIG. 3. The description on the processing function in FIG. 2 will be omitted.

The processing function shown in FIG. 14 has a local area setting portion 63 for setting a local area group 61 from the boundary coordinate point sequence 33 and a mucous boundary determination portion 64 for generating a mucous boundary detection result 62 for the local area group 61.

Next, the determination result of the mucous boundary in the present embodiment will be described referring to FIG. 15.

Figure 15:
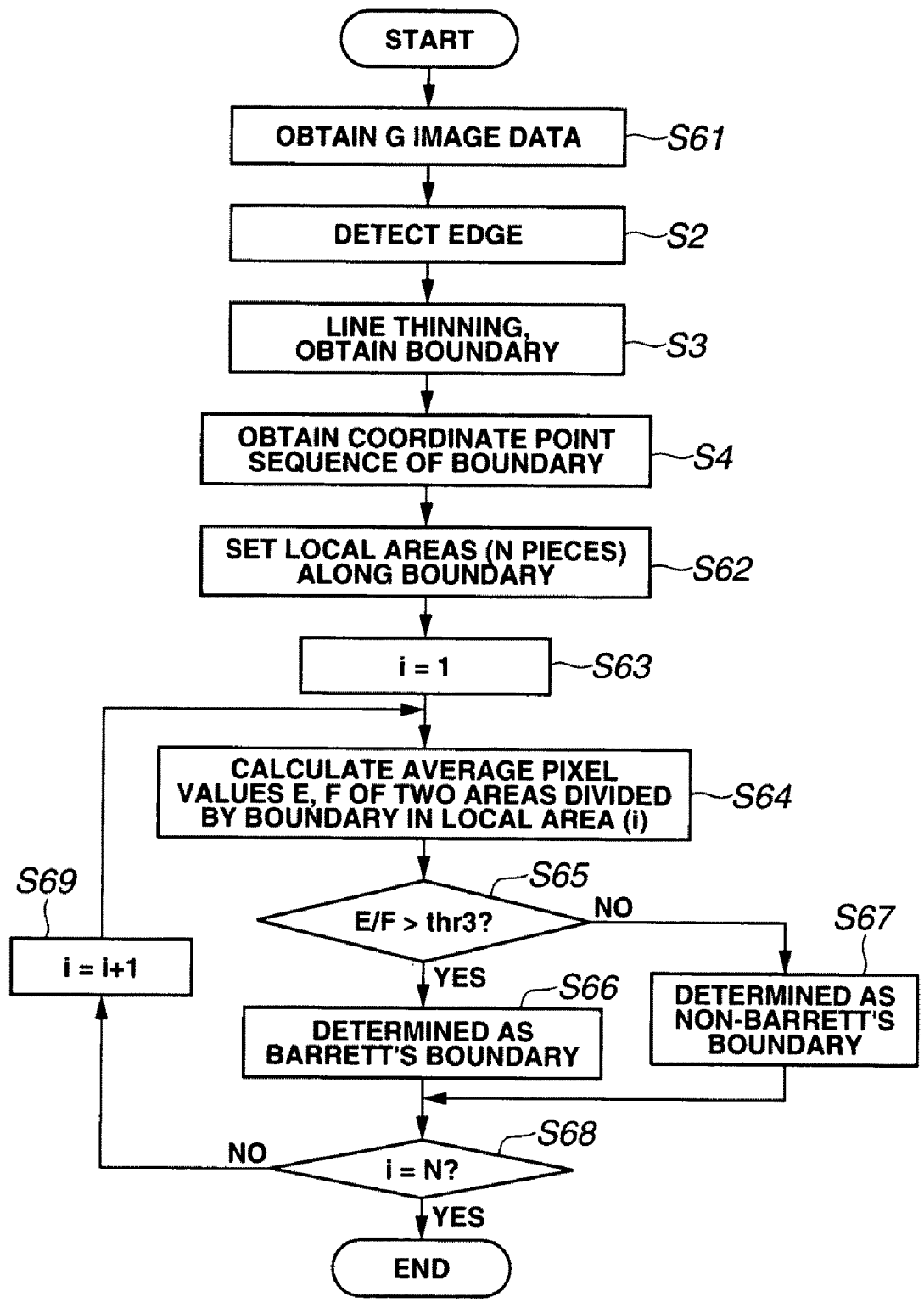
FIG. 15 is a flowchart illustrating a processing procedure processed by the CPU.

As shown in FIG. 15, at the first Step S61, the CPU 22 obtains a G image data, carries out edge detection processing similarly to the first or the second embodiment (S2), applies line thinning and obtains a boundary (S3). Moreover, the coordinate point sequence of the boundary is obtained (S4). Then, the edge detection image in FIG. 16A is obtained.

Next, the processing of a processing program D in FIG. 14 is carried out. That is, as shown in Step S62 in FIG. 15, the CPU 22 sets N pieces of local areas along the boundary, for example. In other words, the local area group 61 made of N pieces is generated.

Figure 16A:
FIG. 16A is a view showing an image in which an edge extracted from the original image is set.
Figure 16B:
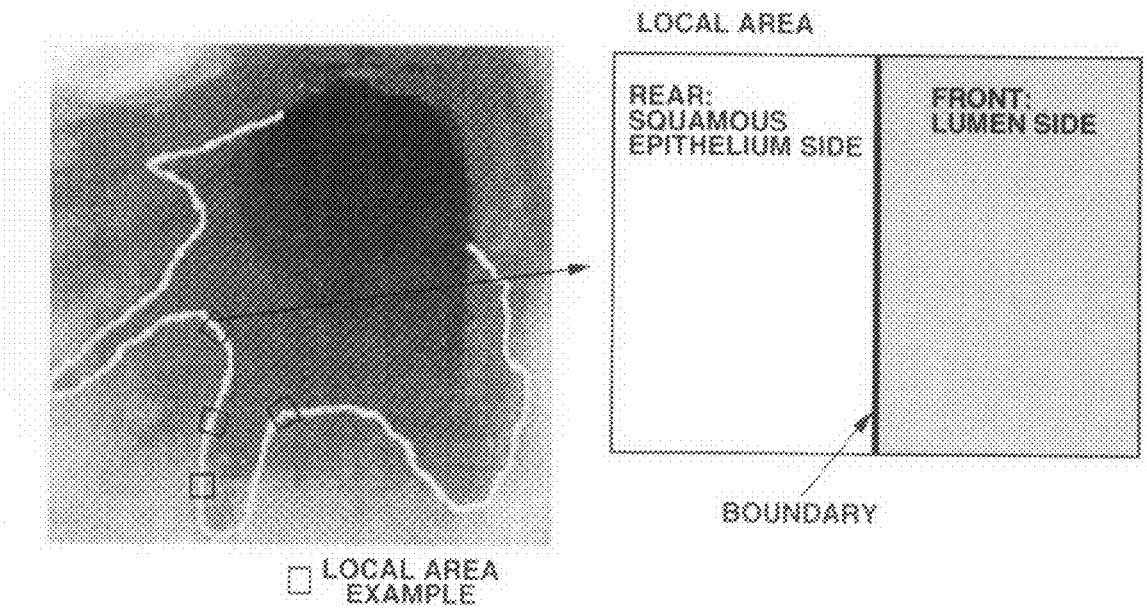
FIG. 16B is a view showing a local area and the like set on the boundary coordinate point sequence of the image in FIG. 16A.

For the boundary coordinate point sequence of the edge detection image in FIG. 16A obtained by the processing till Step S4, a local area is set so that the local area is divided into substantially equal two parts by a short segment (or a tangent) on the boundary as shown in FIG. 16B per predetermined interval, for example, along the boundary in a direction locally orthogonal to the segment (that is, in the gradient direction) on both sides of the short segment on the boundary.

An example of the local area set in FIG. 16B is shown in an enlarged manner in the right. In this case, the local area is set in a rectangular area, but that may be a local area in a circular or any other shape. At the subsequent Step S63, the CPU 22 initializes the parameter i indicating each local area and then, calculates average pixel values E, F of two areas divided along the boundary in the local area (i) at the subsequent Step S64.

At the subsequent Step S65, the CPU 22 determines if the ratio E/F of the average pixels values of the two areas on the both sides divided by the boundary is larger than a predetermined threshold value thr3 or not.

In this case, a tone feature value in the pixel sampled from the Barrett's boundary in a finalized case by diagnosis or an average value of IHb value and an average value of IHb at the pixel sampled from the boundary not being the Barrett's boundary are acquired, and the threshold value thr3 determining distinction between them is determined.

In the case of the ratio of the average pixel values E/F>thr3, at the subsequent Step S66, the CPU 22 recognizes a part of the boundary in the local area as the Barrett's boundary area. On the other hand, if the determination result at Step S65 does not satisfy the determination condition of E/F>thr3, it is determined as not being the Barrett's boundary as shown in Step S67.

After the processing of the above Steps S66, S67, the CPU 22 determines if the parameter i of the local area (i) is equal to N or not at Step S68, and if i is not equal to N, i is incremented by 1 at Step S69, and the routine returns to Step S64, where the processing from Steps S64 to S68 is repeated.

When all the local areas (N) are completed, the processing is finished.

According to the present embodiment as above, determination on the Barrett's boundary or not can be made by determining if the local area set along the boundary is Barrett's boundary or not.

The boundary determination may be made for all the local areas (N) and the boundary may be determined finally by the plurality of determination results.

When the local area is set along the boundary at Step S62, a local area may be set by a segment, two points or the like set symmetrically in a direction orthogonal to the center of a short segment (thin line) on the boundary.

The local area set at Step S62 may be a local area sampled arbitrarily. Also, at the Step S66, the boundary recognized as the Barrett's boundary area is traced and the determination on the Barrett's boundary may be made comprehensively by the results.

Figure 17:
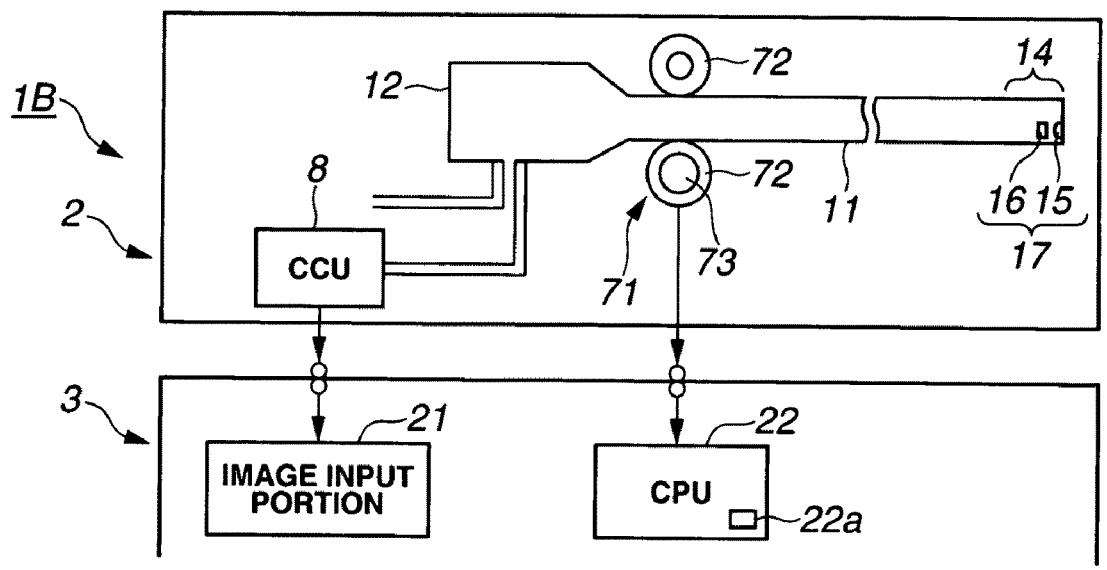
FIG. 17 is a diagram illustrating a major portion of an endoscope system provided with a first variation.

Next, an endoscope system provided with a first variation will be described below. FIG. 17 shows a configuration of an essential part in an endoscope system 1B of the first variation. In this endoscope system 1B, at the proximal end of the insertion portion 11, for example, in the endoscope 6 constituting the endoscope observing device 2 in the endoscope system 1 in FIG. 1, an insertion amount detecting device 71 is provided for detecting an insertion amount by which the insertion portion 11 is inserted into the body cavity. The insertion amount detecting device 71 transmits information on the detected insertion amount to the CPU 22, for example, of the image processing device 3.

The insertion amount detecting device 71 comprises a plurality of rollers 72 rotatably brought into contact with the outer peripheral surface of the insertion portion 11 and a rotating amount detection sensor 73 such as a rotary encoder attached to a single rotating shaft of the rollers 72 for detecting a rotating amount.

A signal detected by the rotating amount detection sensor 73 is inputted to the CPU 22, for example, in the image processing device 3, and the CPU 22 determines if the picked up image is an image including a portion to be detected or not from information of the insertion amount. That is, the CPU 22 has a function of a detection target image determination portion 22a for determining if the picked up image is an image including a portion to be detected.

In this case, when the insertion portion 11 of the endoscope 6 is inserted from the mouth portion of a patient, the position of the tip end portion 14 inserted into the deep side of the esophagus can be detected from a value of the rotating amount detection sensor 73 at the insertion.

Also, whether the image is picked up with a resolution which can be determined by the above-mentioned image processing method or better is determined as one of conditions for determining if the image includes a portion to be detected from the pickup characteristic of the image pickup device 17 including the CCD 16.

That is, an image including a portion to be detected might be obtained from a far place in some cases and if the image is deemed as an image with insufficient resolution for image analysis in the far portion or illumination amount is not sufficient, a determination condition is set so that the image is not determined as an image including a portion to be detected.

An image picked up by the CCD of the endoscope 6 is given signal-processing by the CCU 8 and then, inputted to the image input portion 21 of the image processing device 3 all the time. The images are sequentially stored in a hard disk 27 or the like.

In this case, the CPU 22 stores the information on the insertion amount as information attached to the images sequentially stored in the hard disk 27 or the like. Alternatively, the CPU 22 may store determination information (identification information) obtained by determination on whether the picked up image is an image including a portion to be detected from the information of the insertion amount.

Then, the CPU 22 executes processing similar to the above-mentioned third embodiment for the image including a portion to be determined from the determination information. The processing can be applied not only to the third embodiment but also the first embodiment and the second embodiment.

That is, in the present variation, the original image analyzed in the first to the third embodiments becomes a selected image automatically determined as a detection target form the position determination information.

Therefore, according to the present variation, since the image for determination (detection) by image analysis on whether the characteristic has changed to a feature-changed mucous is limited to the image objectively suited for the preset condition, more objective determination results can be obtained.

Also, since appropriate detection or selection/setting of an image to be detected is possible using the insertion amount detecting device 71 or the like, image processing for an unnecessary image picking up a portion not to be detected can be reduced.

Even for an image picking up a portion to be detected, if the image is far from the image pickup device 17, accuracy by image analysis becomes insufficient. But according to the present variation, by setting a determination condition that the portion to be detected is not picked up when the image is far by more than a predetermined distance, considering the characteristic of the image pickup device 17, accuracy by image analysis can be ensured. In the above description, a case of an image obtained by the endoscope 2 having an elongated insertion portion was described, but an image obtained by using a capsule-type endoscope as will be described below may be used.

Figure 18:
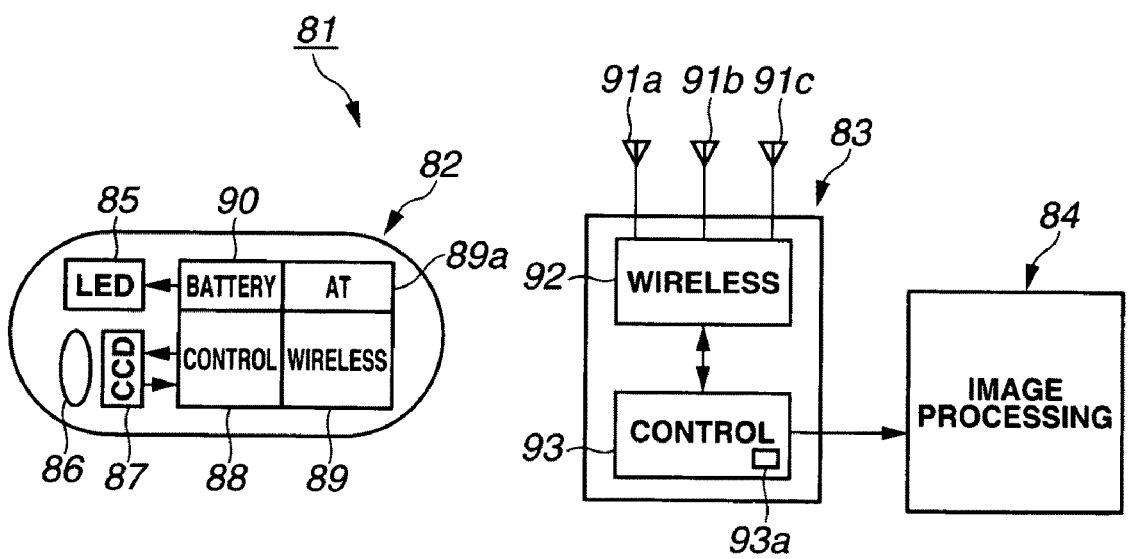
FIG. 18 is a block diagram showing a configuration of a capsule-type endoscope system provided with a second variation.

A capsule-type endoscope system 81 provided with the variation as shown in FIG. 18 comprises a capsule-type endoscope device (hereinafter abbreviated as the capsule-type endoscope) 82 for picking up an image of inside the body cavity by being swallowed by a patient, an in-vitro device 83 arranged outside the body of the patient for receiving and recording image data from the capsule-type endoscope 82, and an image processing device 84 to which an image is inputted from the in-vitro device 83.

The capsule-type endoscope 82 has an LED 85 as illuminating means within a capsule-state container, an objective lens 86 forming an image of an illuminated subject, a CCD 87 arranged at the image forming position and constituting image pickup means for picking up images, a control circuit 88 for signal processing and the like for an image pickup signal picked up by the CCD 87, a wireless circuit 89 for wireless transmission processing of a picked up image, and a battery 90 for supplying power to each circuit and the like.

The in-vitro device 83 receives an electric wave from an antenna 89a of the wireless circuit 89 of the capsule-type endoscope 82 via a plurality of antennas 91a, 91b, 91c, by a wireless circuit 92, and transmits the signal to a control circuit 93. The signal is converted to a video signal by the control circuit 93 and outputted to the image processing device 84.

The image processing device 84 performs processing of each of the above-mentioned embodiments.

The control circuit 93 has a position detection function 93a for estimating a position of the capsule-type endoscope 82 by the plurality of antennas 91a to 91c. The image to be detected may be selected/set using the position detection function 93a. That is, instead of the original image 31, it is determined if a portion close to a boundary from an esophagus to a gaster is picked up or not may be detected by the position detection function 93a, and if the portion close to the boundary is picked up, the image can be utilized as an original image similarly to the above cases.

With such configuration, a living mucous of a portion close to the boundary from an esophagus to a gaster to be detected can be determined efficiently.

In each of the above-mentioned embodiments, IHb value is used as a feature value for tone evaluation, but other feature values such as R/G, R/(R+G+B), for example, may be used. Alternatively, a hue/chroma in an HIS color space may be used, for example.

According to the above-mentioned first to the third embodiments, by detecting presence of a living mucous with different characteristics on the basis of boundary information on the living mucous surface using image processing, a feature-changed mucous such as the Barrett's mucous in which a mucous of an esophagus is changed can be detected.

Fourth Embodiment

Next, an image processing method which can detect a specific living mucous, particularly presence of a Barrett's mucous to be detected more appropriately without being affected by an inappropriate portion such as a dark part in an image referring to FIGS. 19 to 28.

Figure 19:
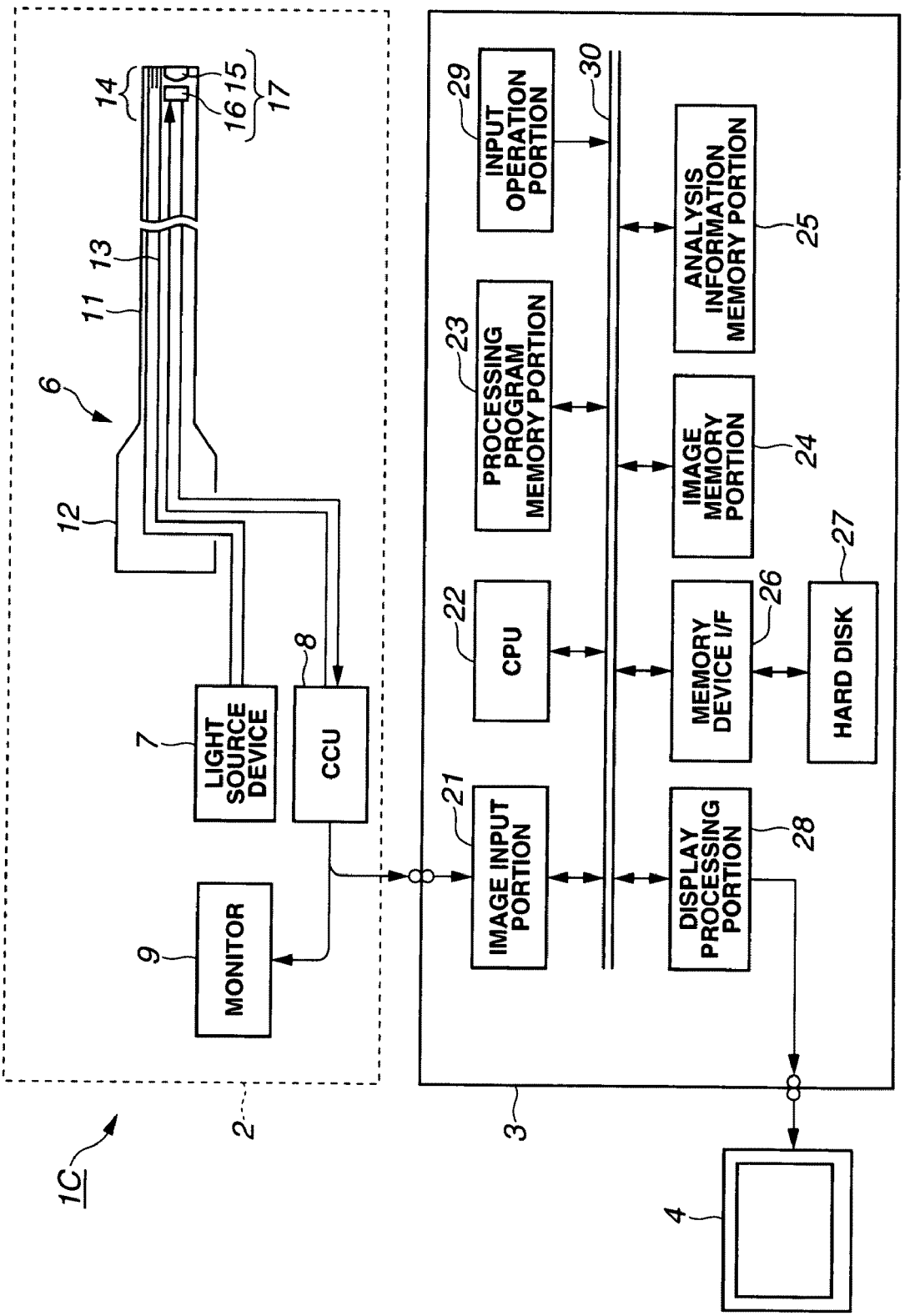
FIG. 19 is a block diagram showing a configuration of an endoscope system provided with a function of an image processing method of a fourth embodiment of the present invention.
Figure 20:
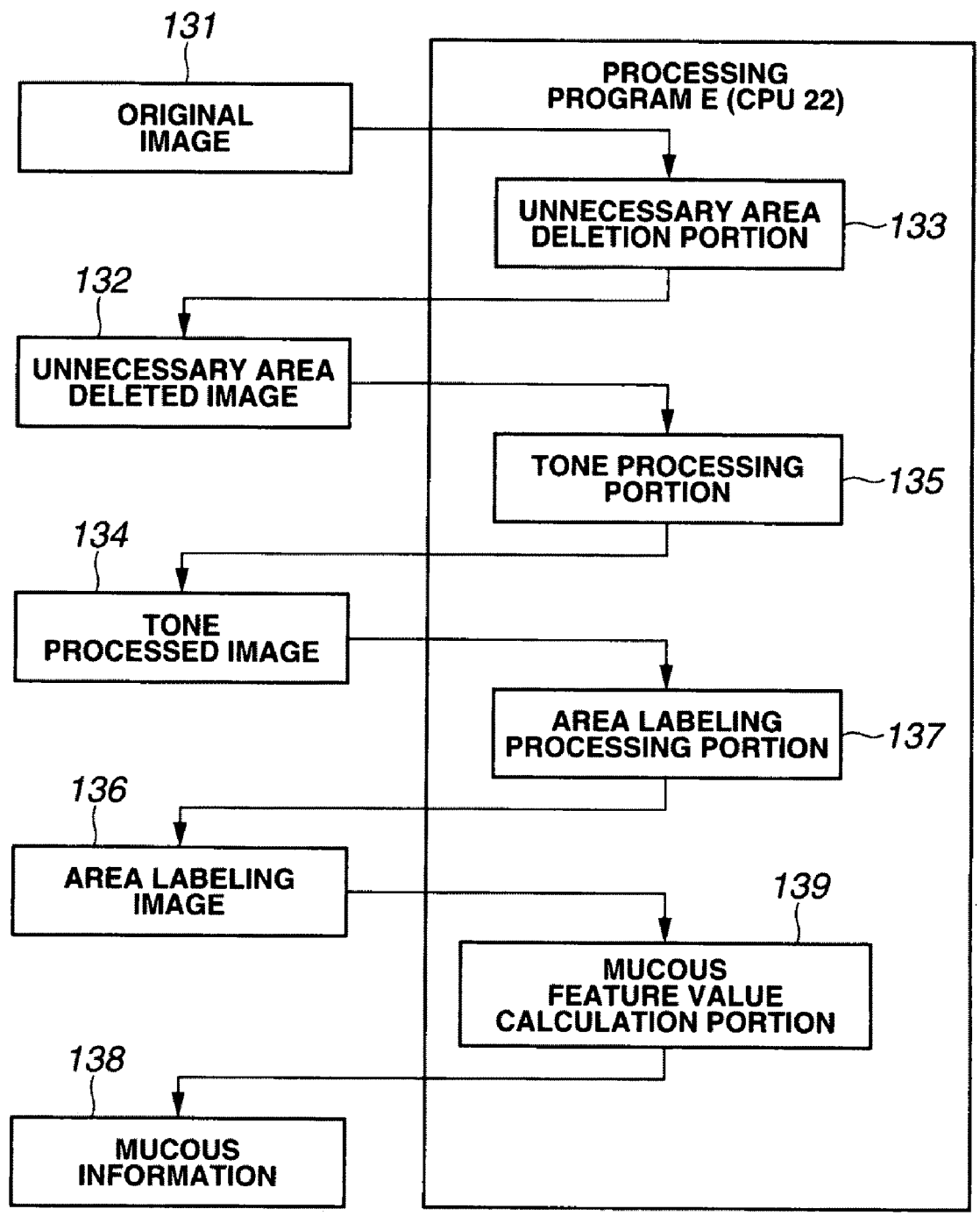
FIG. 20 is a diagram illustrating processing functions to realize the image processing method of the fourth embodiment and images or the like used.

An endoscope system 1C shown in FIG. 19 has the same hardware configuration as that of the endoscope system 1 shown in FIG. 1. However, a processing program E stored in the processing program memory portion 23 in FIG. 19 is different from the processing program stored in the processing program memory portion in FIG. 1. And the CPU 22 executes the processing program E as shown in FIG. 20. Each constituent element in FIG. 19 is given the same reference numerals as the constituent elements shown in FIG. 1, and the description will be omitted.

FIG. 20 is a block diagram illustrating an image processing function for executing image processing for detecting presence of a Barrett's mucous as a mucous tissue to be detected by the CPU 22 according to the processing program E stored in the processing program memory portion 23.

The CPU 22 shown in FIG. 19 has functions of an unnecessary area deletion portion 133 for deleting an unnecessary area from the original image 131 to be processed so as to generate an unnecessary area deleted image 132 and a tone processing portion 135 for tone processing of the unnecessary area deleted image 132 so as to generate a tone processed image 134.

Also, the CPU 22 has functions of an area labeling processing portion 137 for area labeling processing for the image processed image 134 so as to generate an area labeling image 136 and a mucous feature value calculation portion 139 for calculating a mucous feature value of the area labeling image 136 and outputting mucous information 138.

The video signal outputted from the CCU 22 is inputted to the image input portion 21 as an endoscopic image and converted to digital original image data by A/D conversion and reverse γ correction, which is a known technology with a purpose of linear correction, and the CPU 22 executes the following processing according to the processing program.

First, the CPU 22 carries out unnecessary area deletion processing for deleting an unnecessary area from the original image data. The unnecessary area deletion processing generates the unnecessary area deleted image 132 in which an unnecessary area is deleted by replacing pixel values of a pixel unnecessary for determination of mucous tissue type by (0, 0, 0) for the pixel values (R, G, B) of the color original image data. The unnecessary area is a dark part or a halation part with high brightness in an endoscopic image.

Figure 22A:
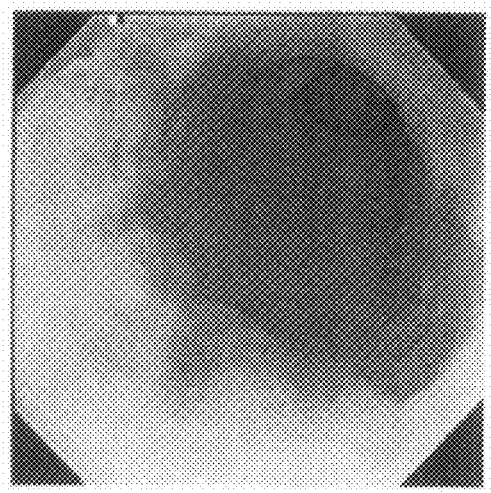
FIG. 22A is a view showing an original image.

FIG. 22A shows a representative example of the original image 131.

Figure 21:
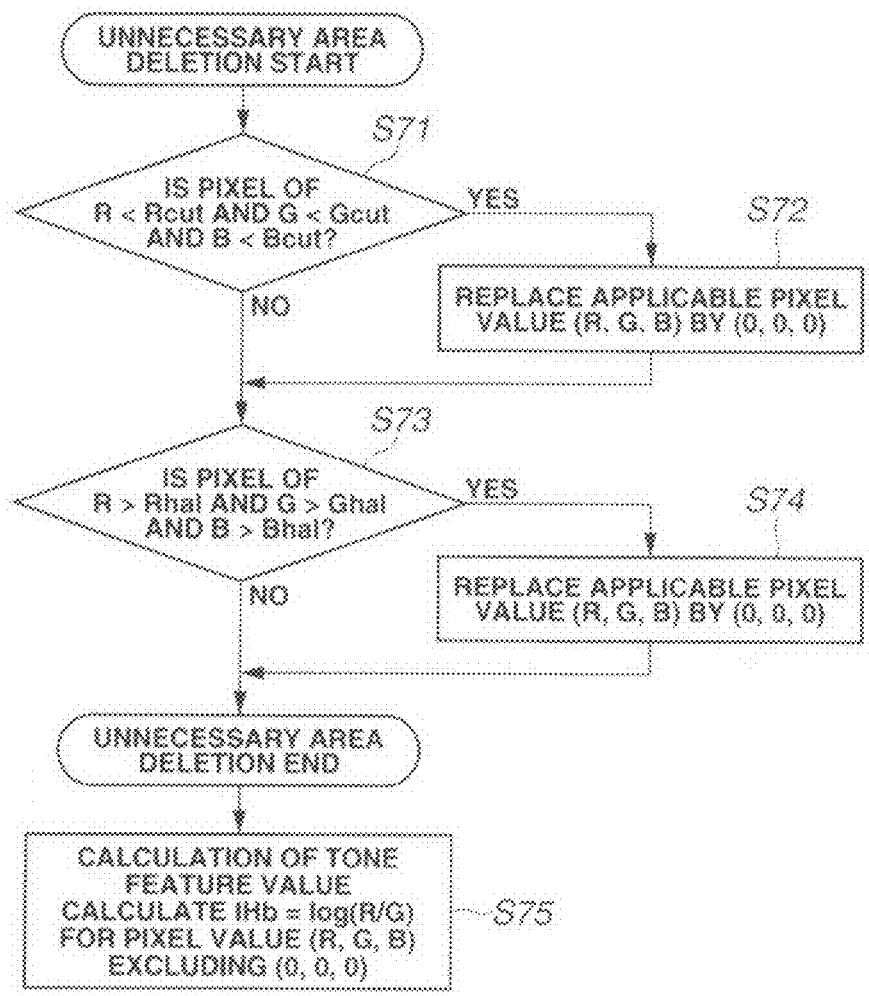
FIG. 21 is a flowchart illustrating processing contents of an unnecessary area deletion processing to delete an unnecessary area.

The unnecessary area deletion processing is shown in FIG. 21. When the processing of unnecessary area deletion is started, as shown in Step S71, the CPU 22 determines if the pixel values (R, G, B) of each pixel constituting the color original image data is a pixel of a dark part or not. An example in which the unnecessary area deletion processing or the like is executed for the unit of a single pixel, but processing for the unit of a plurality of pixels does not deviate from the gist of the present invention, either.

The CPU 22 determines if the pixel is a pixel of R<Rcut and G<Gcut and B<Bcut or not by using threshold values (or reference values) Rcut, Gcut, Bcut for determining if the pixel is a pixel of a dark part or not. The threshold values Rcut, Gcut, Bcut are predetermined values with relatively low brightness values for determining if the pixel is a pixel of a dark part or not and are set by the processing program E.

At Step S71, if there is a pixel applicable to a pixel of a dark part, the CPU 22 replaces the pixel values (R, G, B) of the pixel by pixel values (0, 0, 0) as shown in Step S72, and the routine goes on to the subsequent Step S73.

At Step S71, even if there is no pixel applicable to a dark part, the routine goes on to Step S73.

At Step S73, the CPU 22 determines if the pixel values (R, G, B) of each pixel constituting the color original image data is a pixel of halation or not.

That is, the CPU 22 determines if the pixel is a pixel of R>Rhal and G>Ghal and B>Bhal or not by using threshold values (or reference values) Rhal, Ghal, Bhal for determining if the pixel is a pixel of halation or not. The threshold values Rhal, Ghal, Bhal are predetermined values with relatively high brightness values for determining if the pixel is a pixel of halation or not and are set by the processing program E.

A user such as an operator can change the threshold values Rcut, Gcut, Bcut of the dark point or the threshold values Rhal, Ghal, Bhal of halation from the input operation portion 29.

At Step S73, if there is a pixel applicable to halation, the CPU 22 replaces the pixel values (R, G, B) of the pixel by pixel values (0, 0, 0) as shown in Step S74, and the unnecessary area deletion processing is finished. At Step S73, if there is no pixel applicable to halation, the unnecessary area deletion processing is also finished.

Figure 22B:
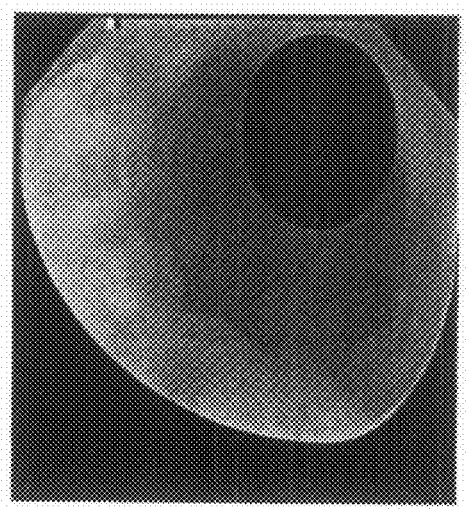
FIG. 22B is a view showing an unnecessary area deleted image generated from the original image in FIG. 22A.

And when the unnecessary area deletion processing in FIG. 21 is finished, the unnecessary area deleted image 132 from which an unnecessary area is deleted is generated. FIG. 22B shows a specific example of the unnecessary area deleted image 132 generated after the unnecessary area deletion processing for the original image 131 in FIG. 22A is finished.

Next, the tone processing portion 135 calculates a tone feature value based on the pixel value for each pixel of the unnecessary area deleted image 132.

However, for the pixels of the pixel values (0, 0, 0) made as the unnecessary area in the processing in FIG. 21, the tone processing portion 135 does not execute calculation processing of the tone feature value.

As a tone feature value, hemoglobin (abbreviated as Hb) index, that is, Hbindex (abbreviated as IHb) having high correlation with a blood flow used in a known technology is used. For the IHb, a brightness signal Vg (G signal reflecting light in the vicinity of 560 nm absorbed by hemoglobin the most) and a brightness signal Vr (R signal reflecting light in the vicinity of 650 nm with least decoration by hemoglobin) per pixel on an endoscopic image are extracted, and a value obtained by logarithm-conversion of the ratio of the two, that is, a calculation formula: $\log_2 (R/G)$ is used. The processing is shown by Step S75 in FIG. 21.

Figure 22C:
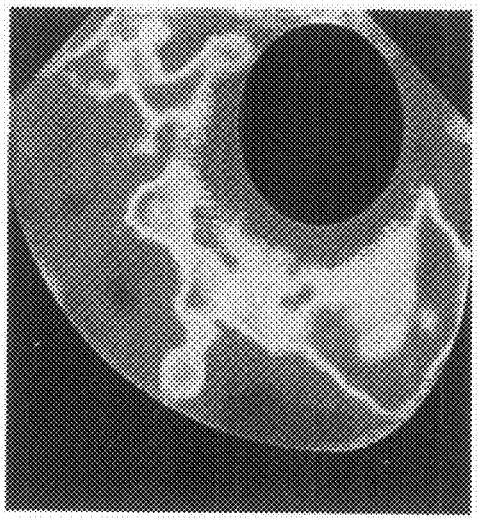
FIG. 22C is a view showing a tone processed image generated by calculation processing of a tone feature value from the unnecessary area deleted image in FIG. 22B.

The tone feature value by the calculated IHb is stored as a pixel value at the same position as the pixel of the original image. For example, the amount is stored in the image memory portion 24 or the analysis information memory portion 25. As above, the tone processed image 134 is generated. FIG. 22C shows an example of the tone processed image 134 after calculation processing of the tone feature value is carried out for the unnecessary area deleted image 132. FIG. 22C is displays a pseudo color image, for example.

In this case, when IHb in the tone processed image 134 is higher than the predetermined threshold value θ, there is a good possibility that the picked up image includes a Barrett's mucous (Barrett's epithelium).

Next, the area labeling processing portion 137 generates the area labeling image 136 for the tone processed image 134 on the basis of a processing flow, which will be described later.

The area labeling image is a labeling image in which the type of an epithelium in the pixel position of the pickup target is stored. In the present embodiment, 1 is stored when the pickup target at the image position is a squamous epithelium of a normal mucous, 2 for the Barrett's mucous as a feature-changed mucous whose characteristic has been changed, and 0 for an unnecessary area.

Figure 23:
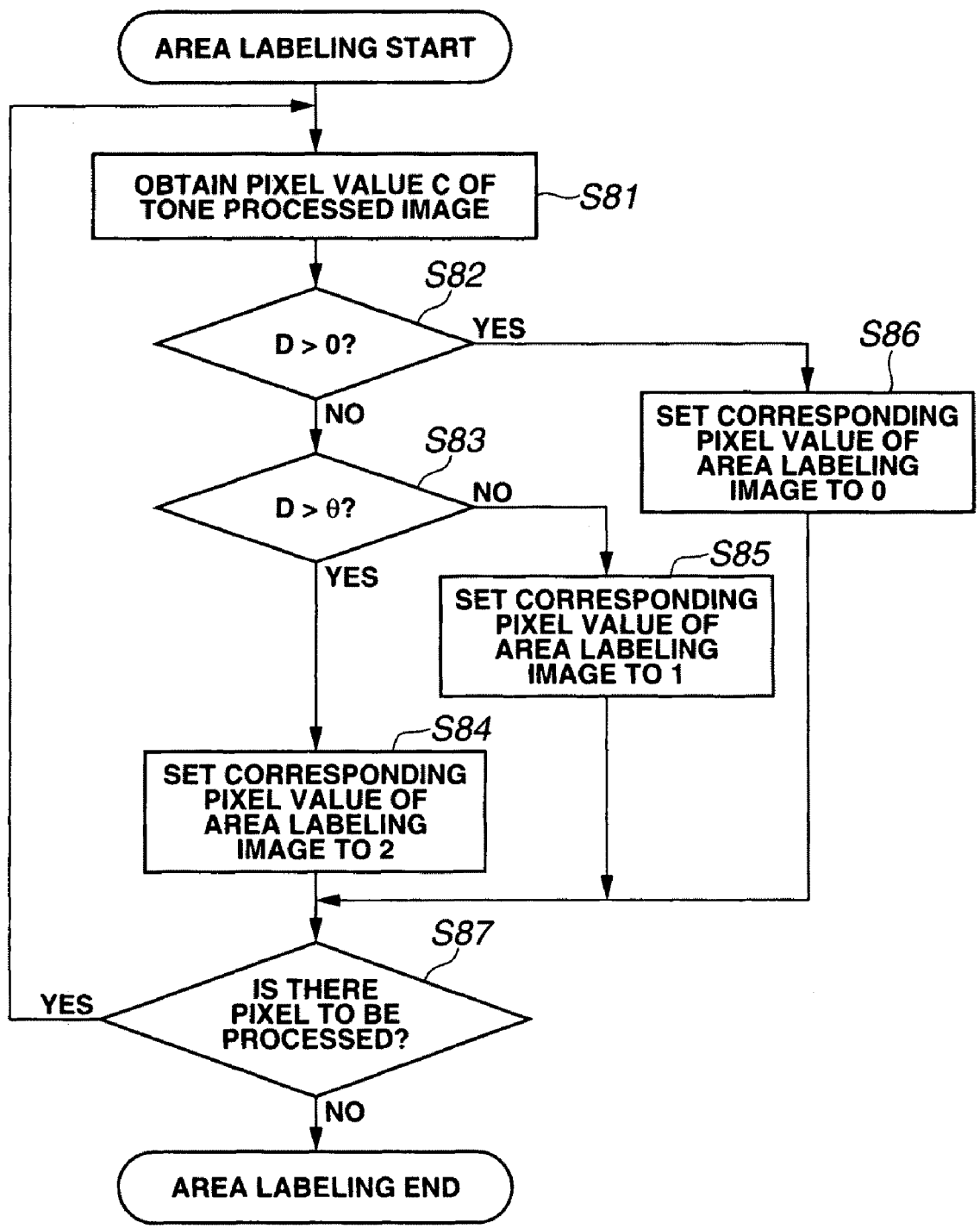
FIG. 23 is a flowchart illustrating processing contents of area labeling.

Next, the processing flow of area labeling will be described referring to FIG. 23.

When the processing flow of the area labeling is started, at the first Step S81, the CPU 22 obtains a pixel value D of a pixel to which labeling processing has not been executed yet from the tone processed image 134.

At the subsequent Step S82, the CPU 22 determines if the pixel value D is 0 or not. If it is determined that the pixel value D is not 0, the routine goes on to the subsequent Step S83, while if the pixel value D is determined as 0, the routine gores on to Step S86.

At Step S83, the CPU 22 compares the size of the predetermined threshold value θ and the above-mentioned pixel value D according to the processing program E. If the determination result is D>θ, the routine goes on to the subsequent Step S84. On the other hand, in the case of D≦θ in the determination of Step S83, the routine goes on to Step S85.

The threshold value θ is set for determination classification from sample data of IHb sampled in advance from a normal mucous and a Barrett's mucous as a feature-changed mucous.

At Step S84, the CPU 22 sets a corresponding pixel value of the area labeling image 136 to 2 and goes on to Step S87. At Step S85, the CPU 22 sets the corresponding pixel of the area labeling image 136 to 1 and goes on to Step S87.

Also, at Step S86, the CPU 22 sets the corresponding pixel value of the area labeling image 136 to 0 and goes on to Step S87.

At Step S87, the CPU 22 determines if there is any pixel for which labeling processing has not been done yet, and if there is an unprocessed pixel, the routine returns to Step S81, while if there is no unprocessed pixel, the area labeling processing is finished.

Figure 22D:
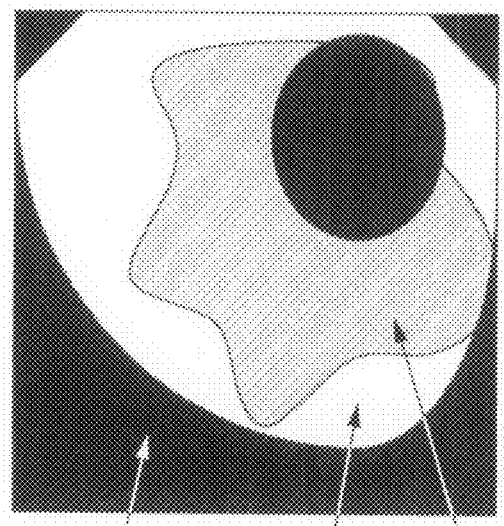
FIG. 22D is a view showing an area labeling image generated from the tone processed image in FIG. 22C.

By the area labeling processing as above, each pixel of the tone processed image 134 is labeled to pixel values 0, 1 or 2 and made into the area labeling image 136. FIG. 22D shows an example of the area labeling image 136.

Next, the mucous feature value calculation portion 139 calculates a mucous feature value of various epithelia for the area labeling image 136.

In the present embodiment, the number of pixels per type of mucous of each epithelium, the boundary pixel point sequence of the area labeling image 136 on the basis of a known boundary line tracing algorithm, and a pixel number ratio of epithelium mucous types (the number of pixels of Barrett's mucous/the number of pixels of squamous epithelium) are acquired and stored as epithelium mucous information.

The mucous feature value calculation portion 139 compares the above-mentioned pixel number ratio of epithelium mucous types and a predetermined threshold value $\tau$ so as to determine presence of a Barrett's mucous, and the determination result is stored as epithelium mucous information. In this case, it is determined that the Barrett's mucous exists in an image when the pixel number ratio by epithelium mucous $\geq \tau$.

On the other hand, in the case of pixel number ratio of epithelium mucous types $<\tau$, it is determined that there is no Barrett's mucous in the image.

Figure 24:
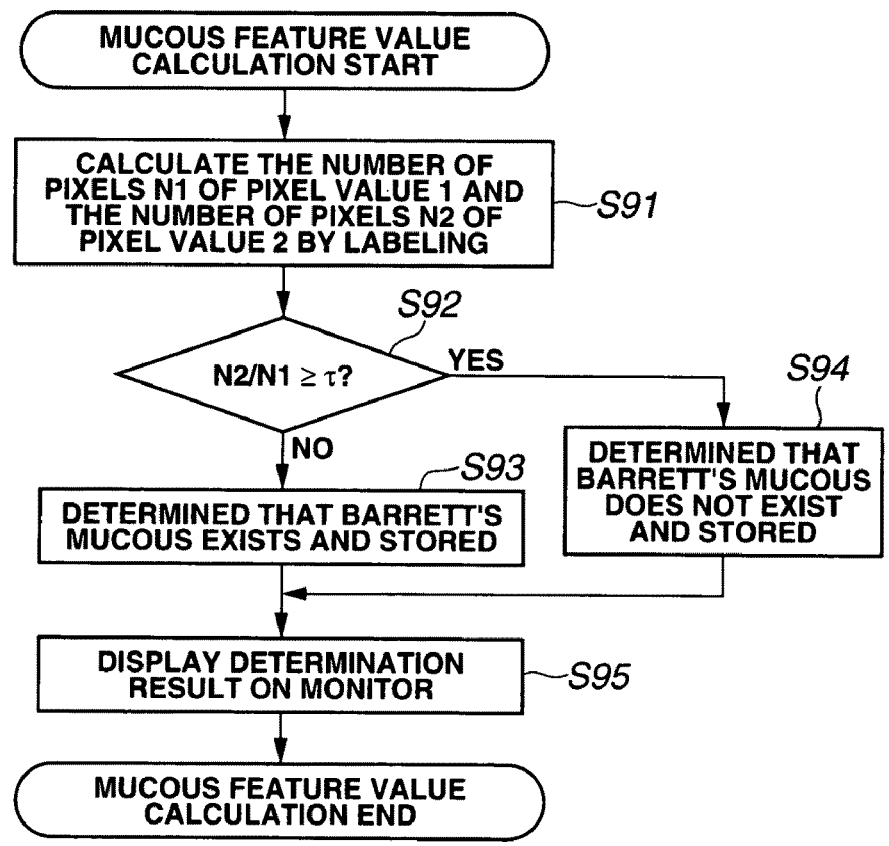
FIG. 24 is a flowchart illustrating processing contents of mucous feature value calculation.

FIG. 24 shows determination processing of the Barrett's mucous by the mucous feature value calculation portion 139.

As shown in Step S91, the CPU 22 counts and calculates the number of pixels N1 of the pixel value 1 labeled as squamous epithelium and the number of pixels N2 of the pixel value 2 labeled as the Barrett's mucous. At the subsequent Step S92, the CPU 22 determines if the pixel number ratio by epithelium mucous type N2/N1 is N2/N1$\geq \tau$ or not by using the threshold value $\tau$ for determining presence of a Barrett's mucous.

When the condition of N2/N1$\geq \tau$ is satisfied by the determination result at Step S92, the CPU 22 determines that there is a Barrett's mucous in the original image as shown in Step S93 and stores the result in the hard disk 27 or the like.

On the other hand, in the case of N2/N1$<\tau$ by the determination result at Step S92, the CPU 22 determines that there is no Barrett's mucous in the original image as shown in Step S94 and stores the result in the hard disk 27 or the like.

After Step S93 and Step S94, the routine goes on to Step S95, where the CPU 22 transmits the determination result to the display monitor 4 via the display processing portion 28 and displays the determination result on the display surface of the display monitor 4. And the processing is finished.

In the above description, the pixel number ratio by epithelium mucous type N2/N1 is used, but N2/(N1+N2) may be employed instead of the pixel number ratio N2/N1. In this case, the determination condition of N2/N1$\geq \tau$ becomes N2/(N1+N2)$\geq (\tau+1)$. That is, determination can be made in the same way even by using the total number of pixels (N1+N2) in the processing target area.

According to the present embodiment as above, whether the Barrett's mucous as a specific living mucous to be detected exists in an image or not is determined by image analysis, and early detection of the Barrett's mucous not relying on subjective judgment is made easy. Also, by displaying the determination result, the better possibility of presence of the Barrett's mucous in the image can be notified to the operator, the operator can make a diagnosis on a feature-changed portion more efficiently.

For the area labeling image 136, expansion/contraction processing as a known technology may be executed immediately after the processing by the area labeling processing portion 137 with the purpose of noise elimination. In the present embodiment, IHb is used as the tone feature value, but other feature values such as R/G, R/(R+G+B) or the like may be used. Also, hue and chroma in an HIS color space, for example, can be used.

Figure 25:
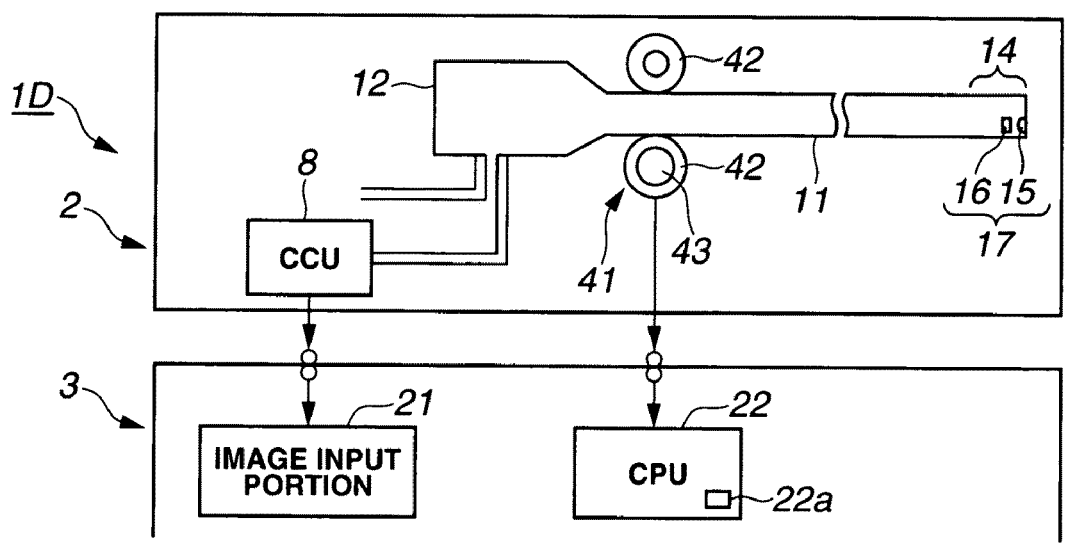
FIG. 25 is a diagram illustrating a part of a configuration of an endoscope system provided with a first variation of the fourth embodiment.

FIG. 25 shows a configuration of an essential part in an endoscope system 1D of a first variation. The endoscope system 1D has, in the endoscope system 1C in FIG. 19, an insertion amount detecting device 41 for detecting an insertion amount by which the insertion portion 11 is inserted into a body cavity provided at the proximal end of the insertion portion 11, for example, in the endoscope 6 constituting the endoscopic observing device 2. The insertion amount detecting device 41 is the same as described in FIG. 17, and the majority of the description will be omitted.

The CPU 22 has the function of the detection target image determination portion 22a for determining if a picked up image is an image including a portion to be detected.

The image picked up by the CCD of the endoscope 6 is signal-processed by the CCU 8 and then, sequentially stored in the hard disk 27 and the like.

The CPU 22 stores the information of the insertion amount as information attached to the image sequentially stored in the hard disk 27 and the like. Alternatively, the CPU 22 may store the determination information (identification information) obtained by determination on whether the picked up image is an image including a portion to be detected as attached information.

The CCU 22 carries out the unnecessary area deletion processing and the like for the image including the portion to be determined from the determination information similarly to the above-mentioned fourth embodiment. That is, in the present variation, the original image given image analysis in the fourth embodiment becomes a selected image automatically determined as detection target by the determination information.

Therefore, according to the present variation, since the image to be analyzed is limited to an image objectively meeting a preset condition, more objective determination result can be obtained.

Also, since an image to be detected can be detected or selected/set appropriately using the insertion portion detecting device 41 or the like, image processing for an unnecessary image picking up a portion not to be detected can be reduced.

Also, if an image of a portion to be detected is located far from the image pickup device 17, accuracy by image analysis becomes insufficient, but according to the present variation, accuracy by image analysis can be ensured by setting a determination condition that a portion to be detected is not picked up when the image is far by a predetermined distance or more, considering the characteristic of the image pickup device 17.

Next, a second variation will be described. The present variation is partially different from the processing program E of the fourth embodiment. The processing function of a CPU 22B for processing according to a processing program F by the variation is as shown in FIG. 26.

Figure 26:
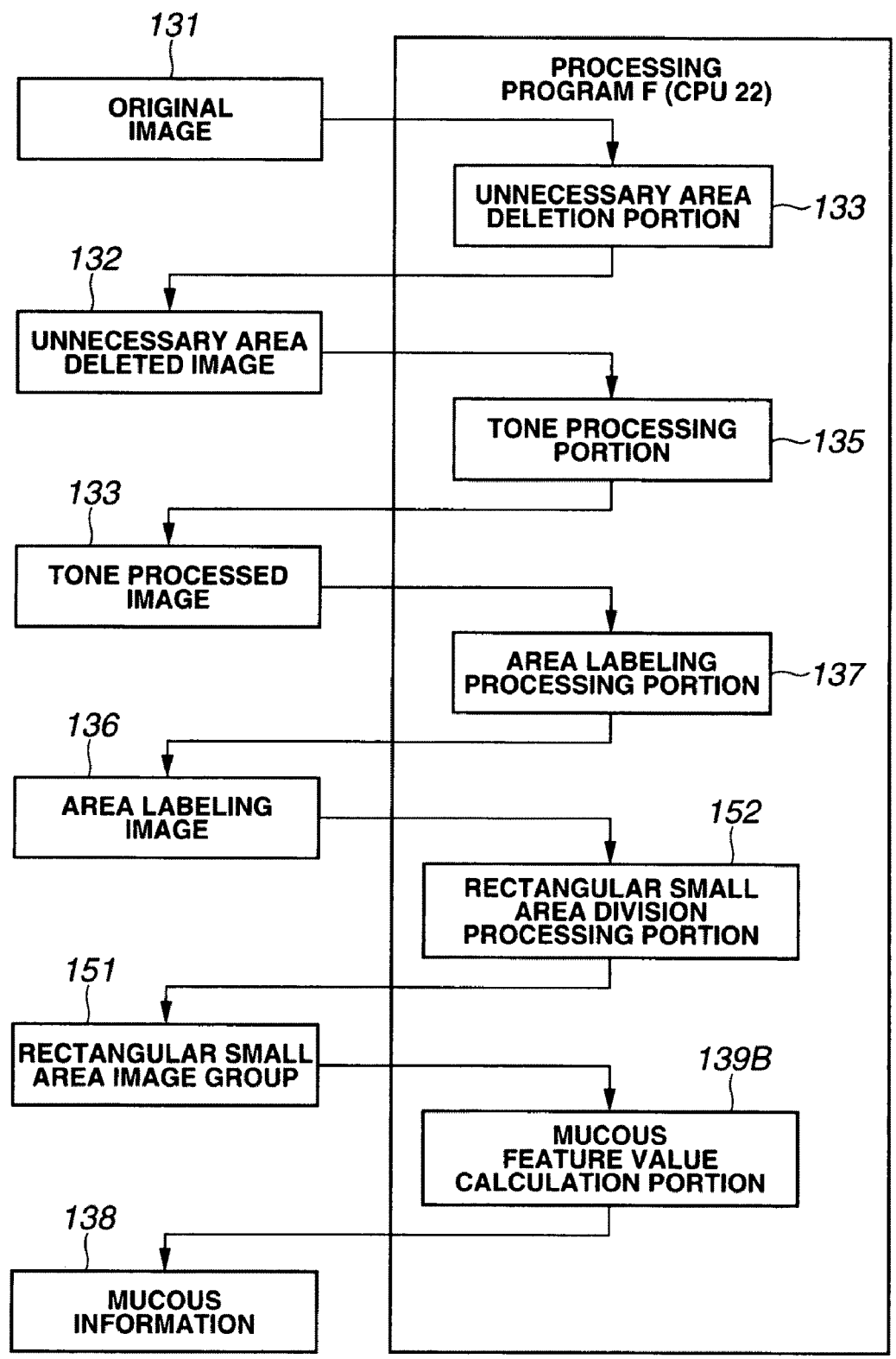
FIG. 26 is a diagram illustrating a processing function to realize an image processing method in a second variation of the fourth embodiment and images or the like used.

The processing function shown in FIG. 26 has, in the processing function of FIG. 20, with respect to the area labeling image 136, a rectangular small area division processing portion 152 for generating a rectangular small area division processing group 151. The rectangular small area division processing portion 152 generates the rectangular small area division processing group 151 by dividing the area labeling image 136.

Figure 27:
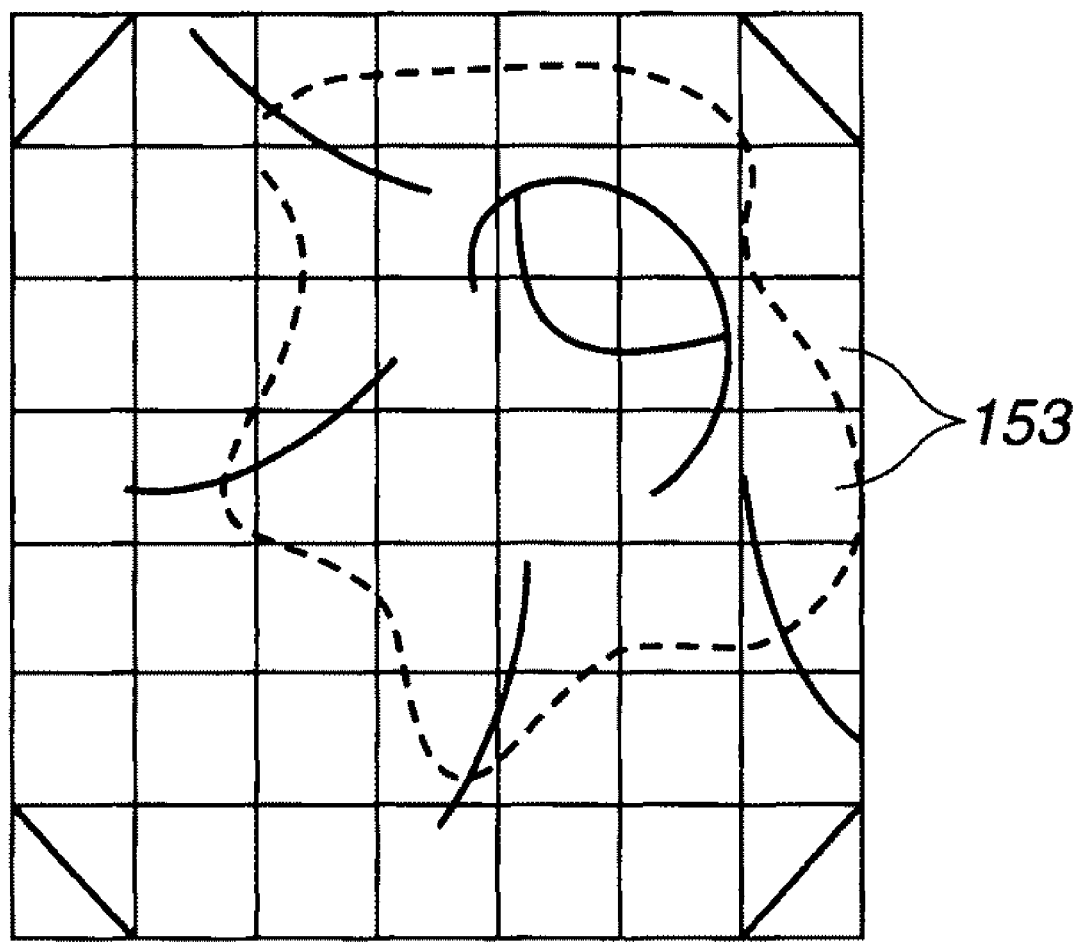
FIG. 27 is a view showing an image example divided into rectangular small areas.

FIG. 27 schematically shows an image of rectangular small areas 153 generated by division.

As shown in FIG. 26, the rectangular small area division processing portion 152 is configured to apply the mucous feature value calculation to the rectangular small area division processing group 151 when the rectangular small area division processing group 151 is generated for the area labeling image 136.

Also, in the present variation, a mucous feature value calculation portion 139B calculates mucous information 138 for each rectangular small area 153 and determines an attribute of the rectangular small area 153 by comparing the pixel number ratio by epithelium mucous type with a preset predetermined threshold value τ.

For example, in the case of the pixel number ratio by epithelium mucous type $\geq \tau$, the attribute of the rectangular small area is determined as a Barrett's mucous. On the other hand, in the case of the pixel number ratio by epithelium mucous type $< \tau$, the attribute of the rectangular small area is determined as squamous epithelium.

The mucous feature value calculation portion 139B counts the number of determined attributes in the rectangular small area 153 and compares the attribute ratio (the number of rectangular small area counts of the Barrett's mucous/the number of rectangular small area counts of the squamous epithelium) and a predetermined threshold value ε.

For example, in the case of the attribute ratio $\geq \epsilon$, it is determined that the Barrett's mucous exists in the image. On the other hand, in the case of the attribute ratio $< \epsilon$, it is determined that the Barrett's mucous does not exist in the image.

Figure 28:
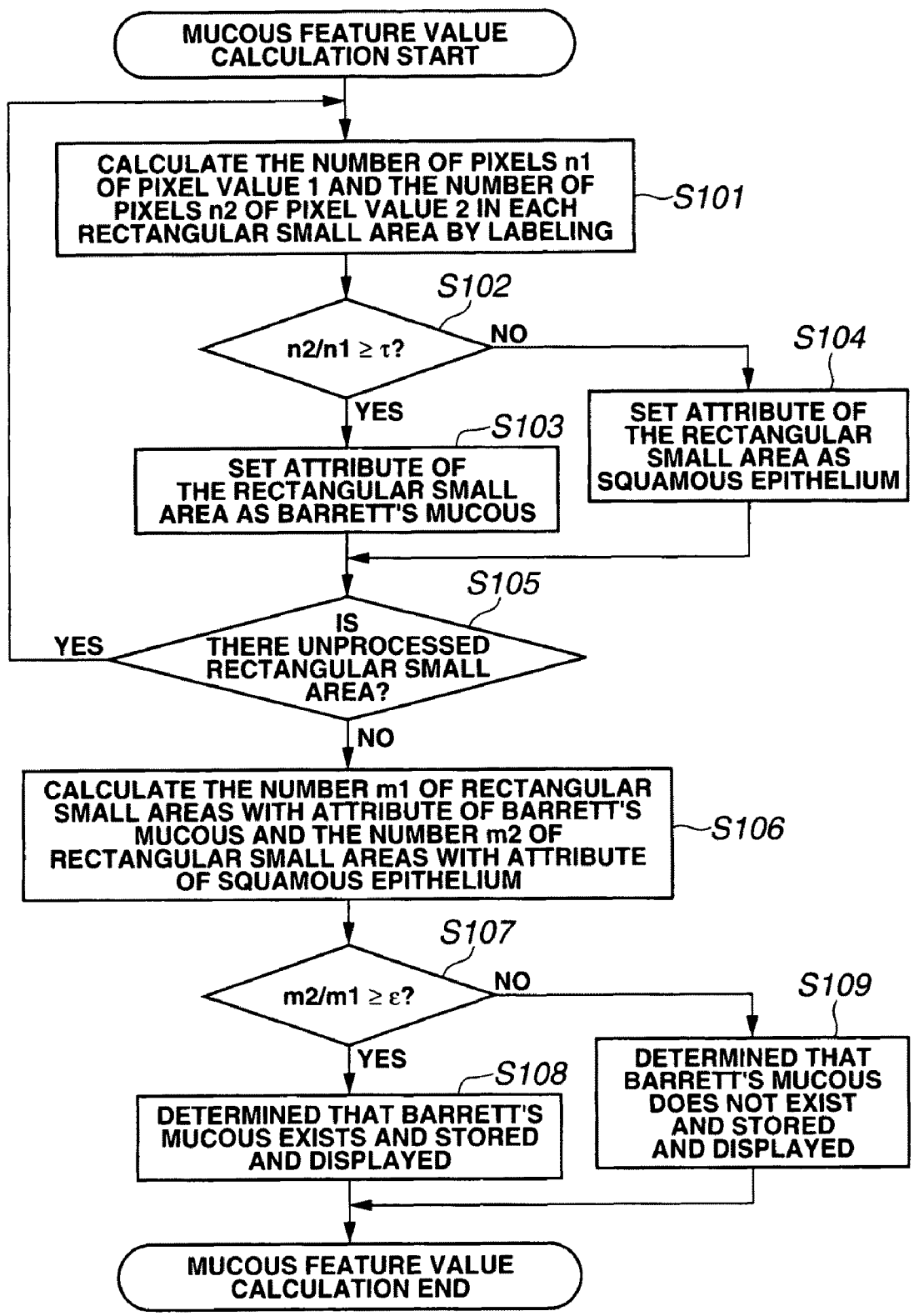
FIG. 28 is a flowchart illustrating processing contents of mucous feature value calculation in the second variation.

FIG. 28 shows a processing flow of the mucous feature value calculation by the mucous feature value calculation portion 139B.

When the processing of mucous feature value calculation is started, as shown in Step S101, the CPU 22 calculates the number of pixels n1 of the pixel value 1 and the number of pixels n2 of the pixel value 2 in each rectangular small area by labeling.

At the subsequent Step S102, the CPU 22 determines if the pixel number ratio n2/n1 is not smaller than a predetermined threshold value τ or not. That is, the CPU 22 determines if $n2/n1 \geq \tau$ or not. And when this condition is met, as shown in Step S103, the CPU 22 sets the attribute of the rectangular small area satisfying the condition as the Barrett's mucous.

On the other hand, if the condition of $n2/n1 \geq \tau$ is not met, as shown in Step S104, the CPU 22 sets the attribute of the rectangular small area as squamous epithelium.

After the processing of Steps S103 and S104, at Step S105, the CPU 22 determines if there is any unprocessed rectangular small area or not and if there is an unprocessed rectangular small area, the routine returns to Step S101 and the processing from Steps S101 to S105 is repeated.

After the processing of Steps S101 to S105 has been completed for all the rectangular small areas, as shown in Step S106, the CPU 22 calculates the number of rectangular small areas m1 with the attribute of the Barrett's mucous and the number of rectangular small areas m2 with the attribute of the squamous epithelium.

At the subsequent Step S107, the CPU 22 determines if the pixel number ratio m2/m1 is not smaller than the predetermined threshold value ε or not. That is, the CPU 22 determines if $m2/m1 \geq \epsilon$. If this condition is satisfied, as shown in Step S108, the CPU 22 determines that there is a Barrett's mucous in the image and stores the determination result in the hard disk 27 and also displays the result on the display monitor 4.

On the other hand, if the condition of $m2/m1 \geq \epsilon$ is not satisfied, as shown in Step S109, the CPU 22 determines that there is no Barrett's mucous in the image and stores the determination result in the hard disk 27 and displays the result on the display monitor 4.

According to the present variation, an image is divided into small areas with some size and whether the small area is an area with a possibility of a Barrett's mucous as a mucous to be detected is determined for each pixel, and determination on the Barrett's mucous or not is further made based on the determination results, and determination on a mucous to be detected can be made more accurately.

That is, in the fourth embodiment, labeling whether there is a possibility of a mucous to be detected is made for each pixel in the entire image, and whether the Barrett's mucous is included or not is determined based on the pixel number ratio by type of the labeling result, and both near portions and far portions are similarly reflected in the determination result of a certain portion.

On the other hand, in this variation, since determination is made for divided small areas, determination in each portion can be made more appropriately, and reliability of the final determination result can be improved.

Fifth Embodiment

Figure 29:
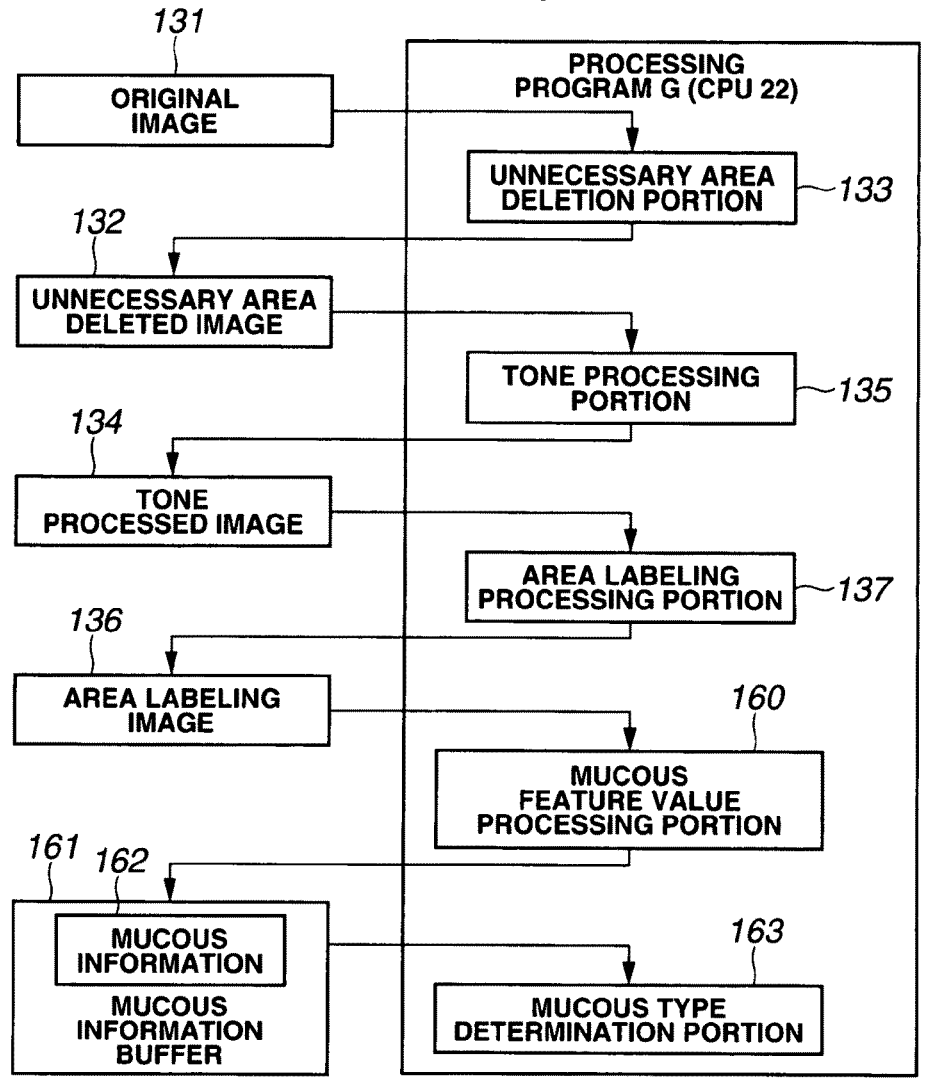
FIG. 29 is a diagram illustrating processing functions to realize an image processing method of a fifth embodiment of the present invention and images or the like used.

Next, a fifth embodiment will be described referring to FIGS. 29 to 31. FIG. 29 shows functional processing contents executed by the CPU 22 on the basis of a processing program G in the fifth embodiment. The present embodiment has the same configuration on hardware as that of the image processing device 3 shown in FIG. 19 and has a processing program G partially different from the processing program E stored in the processing program memory portion 23.

In the present embodiment, the original image is an animation image, for example, and an image of each frame in the animation is sequentially processed.

Those described in the fourth embodiment are shown with the same reference numerals and the description will be omitted.

As shown in FIG. 29, the present embodiment uses a mucous feature value processing portion 160 for calculation processing of a mucous feature value instead of the mucous feature value calculation portion 139 calculating a mucous feature value for the area labeling image 136 in the processing program E in FIG. 20. The mucous feature value processing portion 160 calculates various mucous feature values for the area labeling image 136 and sequentially stores the result in a mucous information buffer 161.

Figure 30:
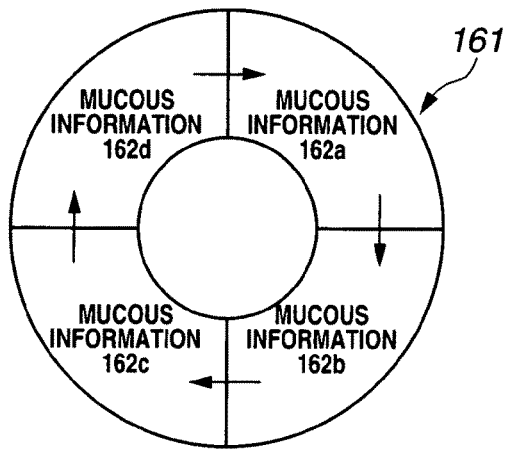
FIG. 30 is a diagram showing a ring buffer storing mucous information.

The mucous information buffer 161 is a ring buffer as shown in FIG. 30, and since the position of the buffer at storing is sequentially moved on a cycle for the next time, when mucous information more than a predetermined number is generated, the mucous information is overwritten on the previously stored mucous information and stored. In an example in FIG. 30, mucous information is stored sequentially in a time series, for example, of mucous information 162a, 162b, 162c, and 162d. When the mucous information is inputted next time, the new mucous information is overwritten on the oldest mucous information 162a. In FIG. 30, 4 pieces of mucous information 162a to 162d are shown, but the ring buffer may have a larger memory capacity.

The mucous feature value processing portion 160 determines presence of a Barrett's mucous in the image from the pixel number ratio by epithelium type of the area labeling image 136 and stores the determination result in the mucous information buffer 161 as mucous information 162.

The mucous type of the mucous information 162 of the mucous information buffer 161 is determined by a mucous type determination portion 163.

Figure 31:
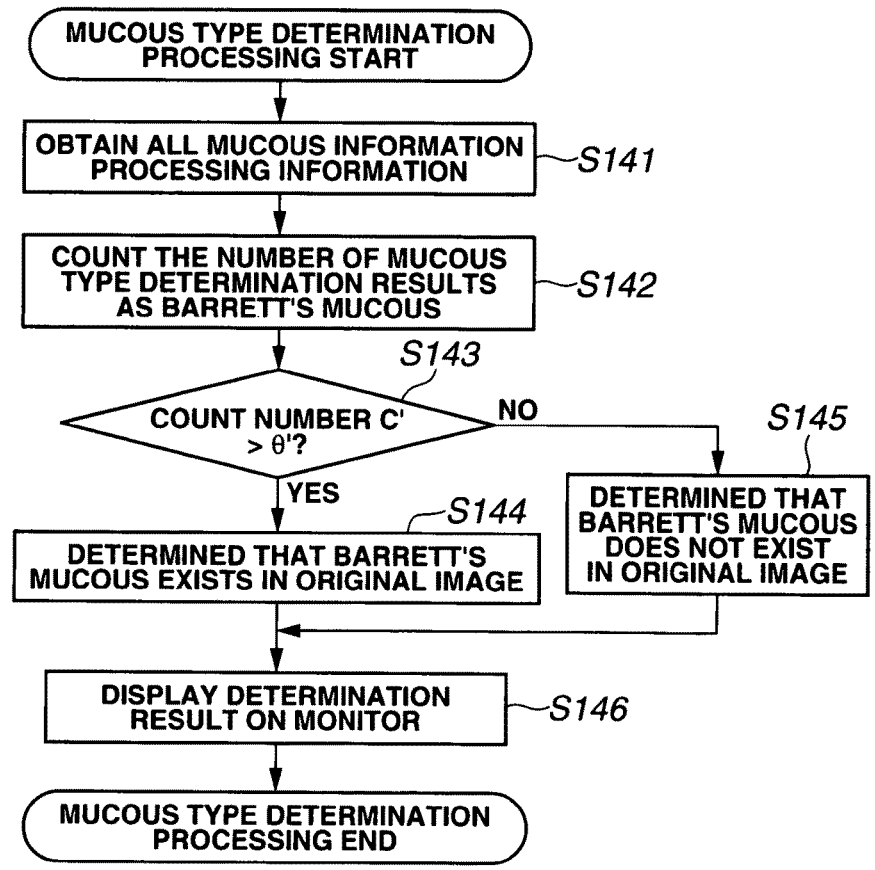
FIG. 31 is a flowchart illustrating mucous determination processing.

A processing flow of the mucous type determination portion 163 is shown in FIG. 31.

At the first Step S141, the CPU 22 obtains all the mucous information 162 stored in the mucous information buffer 161.

At the subsequent Step S142, the CPU 22 counts the number of the mucous type determination results as Barrett's mucous from each of the mucous information 162 and sets the count number as C'.

At the subsequent Step S143, the CPU 22 compares the above-mentioned count number C' with a predetermined threshold value θ' set by the processing program G. That is, it is determined if C'>θ'.

In the case of C'>θ', as shown in Step S144, the CPU 22 determines that there is a Barrett's mucous in the original image.

On the other hand, in the case of C'≦θ', as shown in Step S145, the CPU 22 determines that there is no Barrett's mucous in the original image.

Also, at Step S146 after Steps S144 and S145, the CPU 22 displays the determination result on the display monitor 4 and completes the processing.

In addition to the determination results, the count number C' may also be displayed on the display monitor 4.

According to the present embodiment, since the mucous type is determined from the mucous type results of a plurality of images, misjudgment of the mucous type by an image with poor observing conditions can be prevented.

Also, according to the present embodiment, since presence of a Barrett's mucous can be sequentially determined with an animation image as the original image picked up by the pickup means provided at the tip end portion 14 while inserting the insertion portion 11 of the endoscope 2, the operator can diagnose efficiently (or rapidly) up to the vicinity of a detection target portion from the determination results.

Also, according to the present embodiment, when the insertion portion 11 is inserted from the proximal end to the deep side in an esophagus, if there is a Barrett's mucous in the vicinity of a boundary with a gaster, a probability to display the determination result that the Barrett's mucous exists gets higher, and a diagnosis on the Barrett's mucous can be also made efficiently from the display.

By also displaying the count number C' on the display monitor 4 as above, if there is a Barrett's mucous, the value of the count number C gets larger in general when approaching to the portion where the Barrett's mucous exists, diagnosis on the Barrett's mucous can be made efficiently from the display.

Instead of continuous input of frames of an animation image, the original image may be inputted with a given frame interval.

Also, when the number of pixels of the pixel value=0 included in the area labeling image 136 is larger than a predetermined threshold value at the mucous characteristic processing portion 160, it may be so configured that the mucous information 162 is not stored and information inappropriate for determination of mucous type is not stored.

Sixth Embodiment

Next, a sixth embodiment will be described referring to FIGS. 32A to 37. The present embodiment has an object to provide an image processing method which can detect (determine) presence of a detection target mucous with accuracy. In order to achieve the object, a small area inappropriate for detection such as a dark part in an image is detected and excluded from detection target, position information of the dark part in the image is referred to from the detection result, and those adjacent to the dark area and determined as a small area to be excluded are further excluded from the detection target and processing for generating an image of a processing target area is carried out.

Figure 32A:
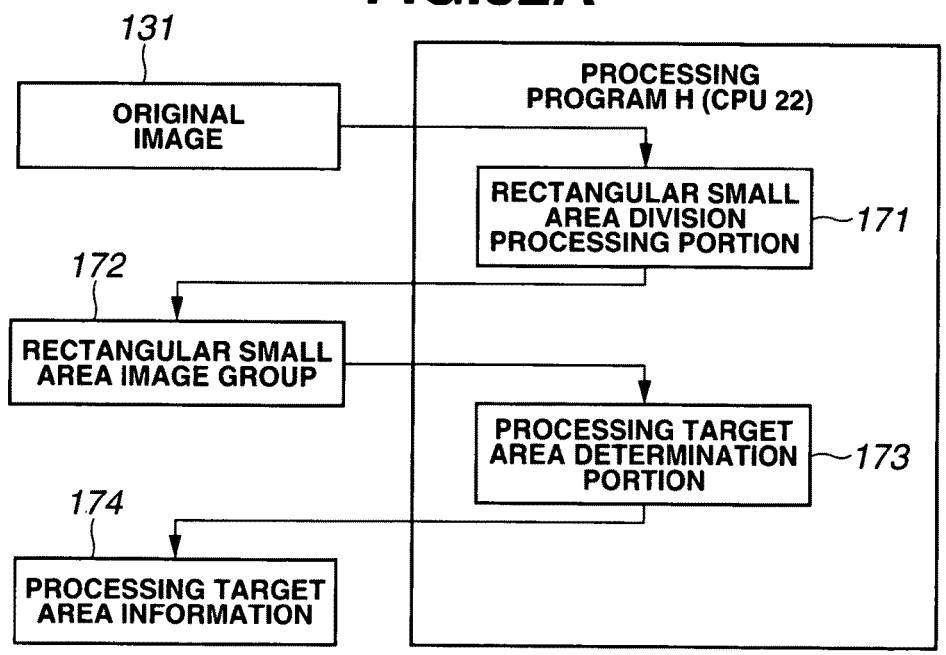
FIG. 32A is a diagram illustrating a processing function to realize an image processing method of a sixth embodiment of the present invention and images used.

FIG. 32A shows functional processing contents executed by the CPU 22 on the basis of a processing program H in the sixth embodiment. The present embodiment has processing programs H and I which have the same configuration on hardware as the image processing device 3 shown in FIG. 19 and are partially different from the processing program E stored in the processing program memory portion 23.

Figure 32B:
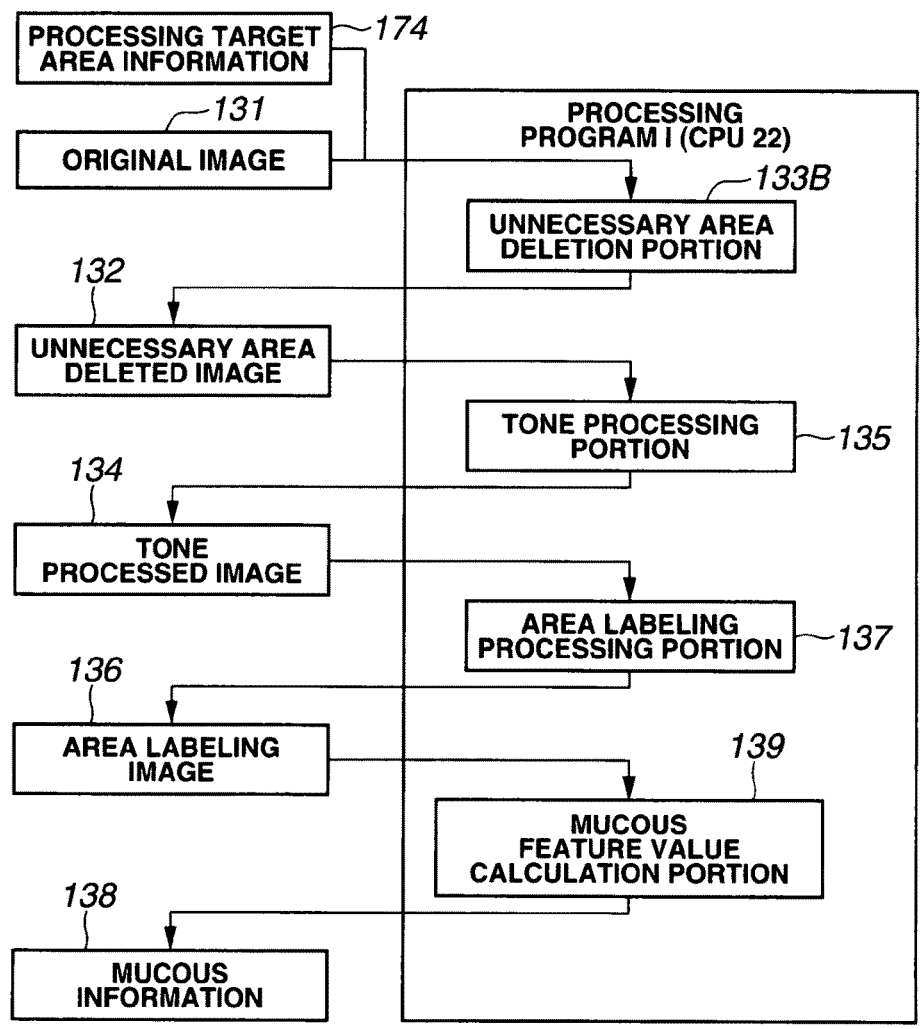
FIG. 32B is a diagram illustrating a processing function to realize an image processing method after processing in FIG. 32A and images or the like used.
Figure 33:
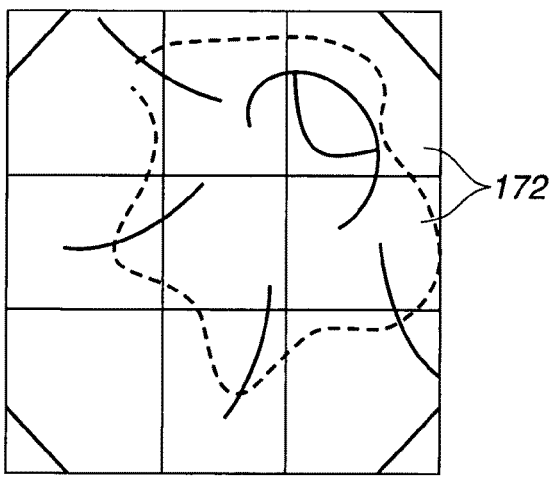
FIG. 33 is a view showing an image divided into rectangular small area groups.

The mucous type determination processing in the present embodiment is configured to continuously execute the processing program H shown in FIG. 32A and the processing program I shown in FIG. 32B. The processing program I uses processing target area information 174, which is the result of the processing program H.

A processing block of the processing program H characterizing the present embodiment will be described.

The original image 131 is inputted to a rectangular small area division processing portion 171, and the rectangular small area division processing portion 171 divides the endoscopic image into rectangular small area image groups 172. The small areas are not limited to rectangular.

Figure 34:
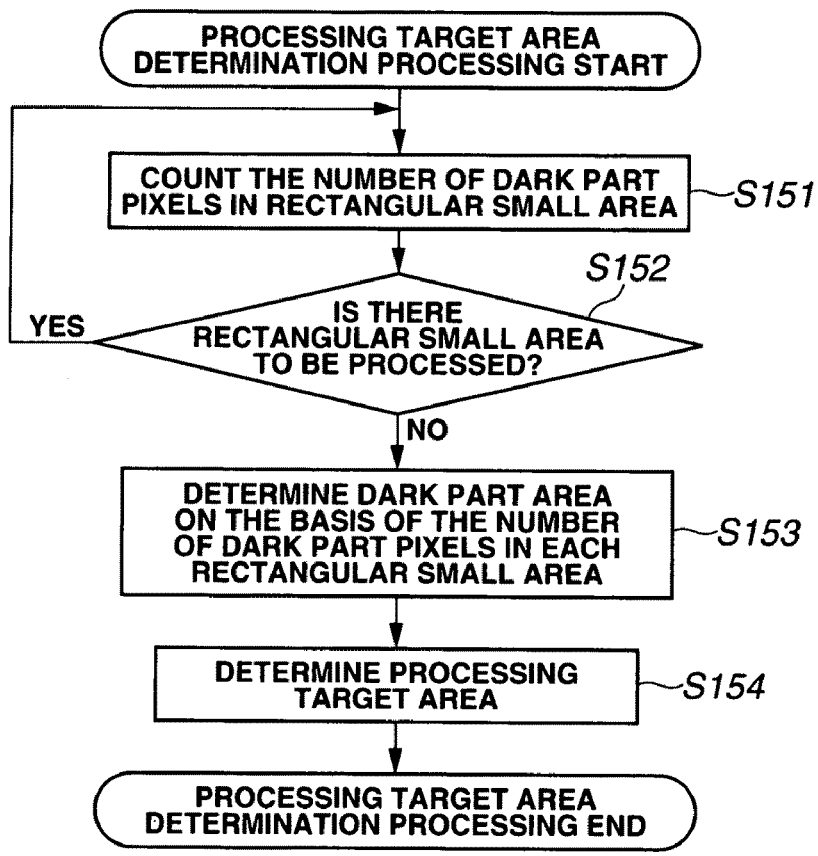
FIG. 34 is a flowchart illustrating processing contents of processing target area determination.

The rectangular small area image groups 172 are inputted to a processing target area determination portion 173, and the processing target area determination portion 173 executes the processing shown in the flow in FIG. 34 and generates processing target area information 174.

At step S151, the processing target area determination portion 173 obtains a rectangular small area 175 from the rectangular small area image groups 172 and counts the number of dark-part pixels in the rectangular small area 175 in order to detect a small area to be excluded from processing targets.

In the present embodiment, the dark-part pixels are pixels with R<Rcut and G,<Gcut and B<Bcut. The count number is set as Cn (where, n denotes a serial number of the rectangular small areas). Rcut and the like are those described in the fourth embodiment. They may be set to threshold values different from those in the fourth embodiment.

At Step S152, the processing target area determination portion 173 determines if there is a rectangular small area 175 to be processed (not processed at Step S151 yet) or not, and if there is the rectangular small area 175 to be processed, the routine returns to Step S151, where the count processing is executed. If there is not the rectangular small area 175 to be processed, the routine goes on to Step S153.

At Step S153, the processing target area determination portion 173 executes determination processing of a dark-part area to be excluded from the processing target on the basis of the dark-part pixel number Cn of the rectangular small area 175. The determination in the present embodiment determines the rectangular small area 175 with the maximum Cn calculated for each rectangular small area 175 as a dark-part area.

Next, at Step S154, the processing target area determination portion 173 excludes the dark-part area from the processing target areas and moreover, determines the processing target area on the basis of the position of the dark-part area in the original image 131.

The determination method will be described using FIG. 35.

Figure 35:
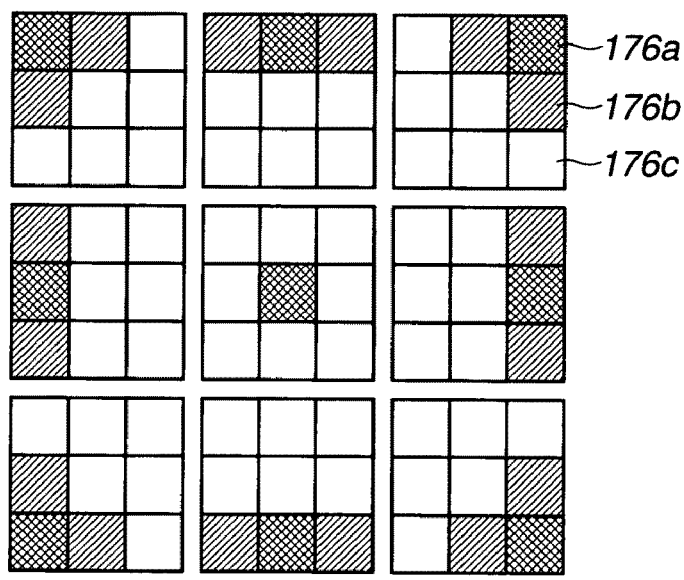
FIG. 35 is an explanatory diagram when a processing target area is determined on the basis of a detected dark part area.

A double shaded portion (cross shaded portion) 176*a* in FIG. 35 indicates the dark-part area determined at Step S153, and all the patterns which can be realized when the area is divided into 3×3, that is, 9 small areas are enumerated. A shaded portion 176*b* indicates a small area to be excluded from the processing target.

At Step S154, the processing target area determination portion 173 determines to which pattern in FIG. 35 the dark-area corresponds according the position of the dark-part area in the original image 131. And the processing target area determination portion 173 determines only the small areas excluding the dark-part area and the small area excluded from processing as processing targets according to the applicable pattern.

Figure 36:
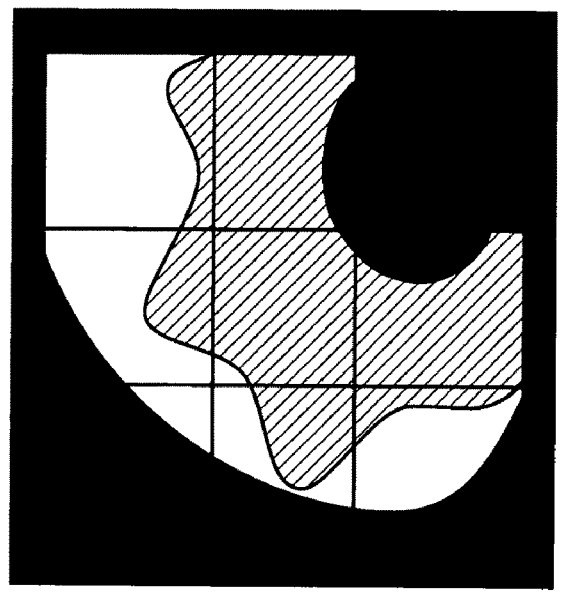
FIG. 36 is a view showing an image example of the detected dark part.

For example, when an upper right corner is detected as a dark part as shown in FIG. 36, two adjacent portions on the both sides of the double shaded portion 176*a* are excluded as shown in the uppermost pattern on the right in FIG. 35.

And the processing target area information 174 is generated with a small area 176*c* to which no shading is given as a processing target other than the double shaded portion 176*a* and the shaded portion 176*b* in FIG. 35. That is, from the information of the detected double shaded portion 176*a*, the processing target area information 174 is generated (determined).

Therefore, in the memory means such as the processing program memory portion 23 and the analysis information memory portion 25, excluded-block information determining a block to be excluded from the processing target is registered (stored) according to the block position of the block of a dark-part area detected in advance (small area) in the original image 131. Specifically, a plurality of patterns are stored as excluded-block information as shown in FIG. 35. And by referring to the excluded-block information, the processing target area can be determined according to the position of the dark-part area.

An unnecessary area deletion portion 133B in the processing program I in FIG. 32B generates an unnecessary area deleted image 132 in which the pixels not to be processed are replaced by (R, G, B)=(0, 0, 0) by using the above processing target area information 174.

The subsequent processing is the same as the generation processing contents of the mucous information in FIG. 20, for example.

In the processing target area determination portion 173, it may be so configured that the number of pixels with R=255 in the processing target area is counted for each small area 175 and when the number of pixels with R=255 becomes larger than a predetermined number of pixels, it is considered to be too close to the target to be picked up and the small area 175 is excluded from the processing target area.

Also, the size (the number of pixels) of the small area 175 may be able to be selected/set. Alternatively, depending on the size, a plurality of dark parts are detected and the portion around them may be excluded from the processing target area depending on the arrangement, distribution or the like. When configured in this way, the processing target area can be set more appropriately.

According to the present embodiment, since not only the small areas including a dark part but also the small areas adjacent to the dark part are determined if they are small area inappropriate for processing or not so that the inappropriate small areas are excluded from the processing target, the remaining areas are more appropriate for detection target and thus, detection accuracy (determination accuracy) of a specific living mucous can be further improved.

Explaining supplementarily, when a dark-part area and areas close to the dark-part area are distributed concentrically or in other shapes according to a portion in the body cavity, if a dark part is detected only by setting the small area 175, there is a possibility that the actual dark part and areas close to the dark part can not be surely excluded from the detection target.

Even in this case, the areas not appropriate for detection target can be excluded efficiently and appropriately from position, arrangement or distribution of the dark-part area detected as above. The dark-part pixel or the like can be excluded for each pixel but that would take time. On the other hand, the exclusion is carried out for blocks in the present embodiment, and inappropriate blocks can be excluded efficiently.

In the above description, a case of an image obtained by the endoscope 2 having an elongated insertion portion is used, but an image obtained by using a capsule-type endoscope as will be described below may be utilized.

Figure 37:
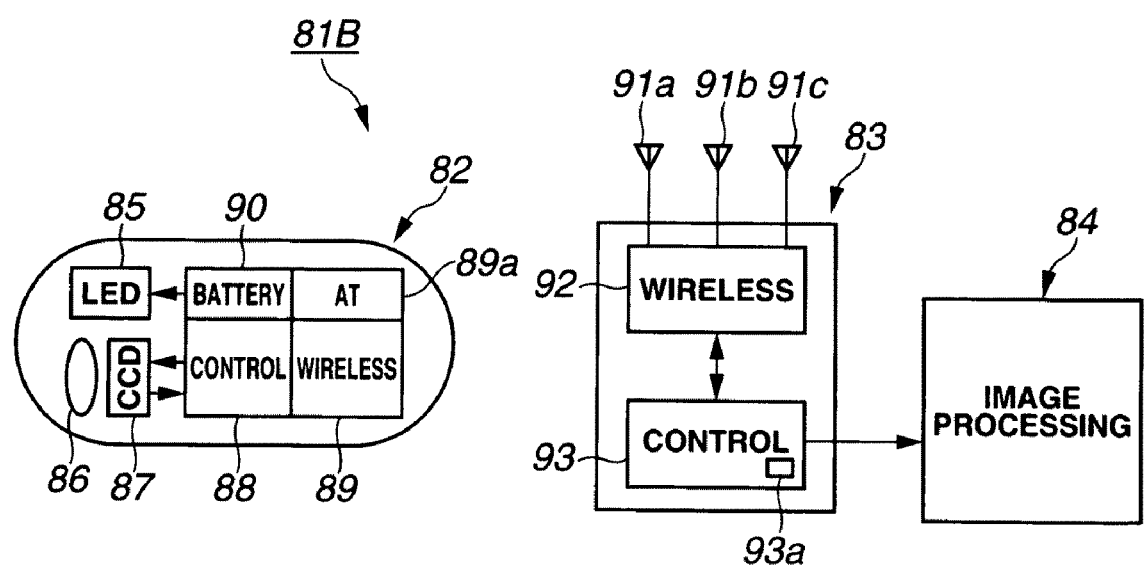
FIG. 37 is a block diagram showing a configuration of a capsule-type endoscope system provided with a capsule-type endoscope in a variation of the sixth embodiment.

A capsule-type endoscope system 81B provided with a variation as shown in FIG. 37 has the same configuration on hardware as in FIG. 18. Thus, the description of the configuration will be omitted.

An image processing device 84 executes the image processing of one of the above-mentioned fourth embodiment to the sixth embodiment.

According to the fourth to the sixth embodiments, by excluding pixels inappropriate for detection target such as a dark part, presence of a specific living mucous to be detected can be detected more accurately.

Embodiments comprised by partially combining each of the above-mentioned embodiments or changing the order of processing steps also belong to the present invention.

Having described the preferred embodiment and modification of the invention referring to the accompanying drawings, it should be understood that the present invention is not limited to the precise embodiment and modification and various changes and modifications thereof could be made by one skilled in the art without departing from the spirit and scope of the invention as defined in the appended claims.

What is claimed is:

1. A medical image processing method for image processing of a medical image depicting a living mucous, the method comprising:
    a boundary detecting step for detecting a boundary of the living mucous from the medical image;
    a mucous feature detecting step for detecting an outline configuring a boundary between an esophagus mucous and a gastric mucous with a different feature on the basis of the boundary detected at the boundary detecting step;
    a refraction point calculating step for calculating a refracted refraction point on the outline;
    an outline shape extracting step for extracting information on a shape of the boundary between the esophagus mucous and the gastric mucous, based on information of the refraction point on the outline calculated at the refraction point calculating step; and a determining step for determining whether or not the shape of the boundary is complicated, based on the information on the shape of the boundary between the esophagus mucous and the gastric mucous, which is detected at the outline shape extracting step, in order to determine whether or not a squamous epithelium of an esophagus is replaced by the gastric mucous.

2. The medical image processing method according to claim 1, further comprising an input step for inputting one or more medical images picking up an image of the living mucous into an image processing device for detecting the boundary.

3. The medical image processing method according to claim 1, further comprising an isolated area detecting step for detecting an isolated area existing locally in one of the areas and isolated from the other areas from the boundary detected at the boundary detecting step.

4. The medical image processing method according to claim 1, further comprising:
   an area setting step for setting a local area including the boundary on the basis of the boundary detected at the boundary detecting step; and
   a feature value calculating step for calculating a feature value from two areas on the both sides of the boundary in the local area.

5. The medical image processing method according to claim 1, wherein the boundary detecting step includes a binarization step for binarization and a line thinning step for generating a line-thinned mucous boundary image.

6. The medical image processing method according to claim 1, wherein the outline shape detecting step detects presence of a living mucous with a different characteristic based on whether one or more refracted refraction points are detected from the boundary shape in the boundary.

7. The medical image processing method according to claim 1, wherein the outline shape detecting step includes a filtering step applying filtering for extracting information on the shape of the boundary between the esophagus mucous and the gastric mucous.

8. The medical image processing method according to claim 1, wherein the mucous feature detecting step detects presence of a Barrett's mucous in the vicinity of the boundary between the esophagus mucous and the gastric mucous as a living mucous with different feature.

9. The medical image processing method according to claim 4, wherein the isolated area detecting step has a determination step for determining if the detected isolated area is the same type of mucous as the mucous in the other areas.

10. The medical image processing method according to claim 9, wherein the determination step has a feature value calculating step for calculating a feature value relating to a brightness or a tone of a mucous in the other area for the detected isolated area.

11. The medical image processing method according to claim 10, wherein the determination step has a comparison step for comparing the calculated feature value with a threshold value.

12. The medical image processing method according to claim 1, wherein the medical image is an endoscopic image or a capsule-type endoscopic image.

13. The medical image processing method according to claim 1, further comprising an isolated area detecting step for detecting an isolated area existing locally in one of the areas which is a side of the gastric mucous and isolated from the other areas which is a side of the esophagus mucous, from the boundary detected at the boundary detecting step.

14. The medical image processing method according to claim 1, wherein the boundary detecting step detects a boundary on which the esophagus mucous and the gastric mucous are adjacent to each other.

15. The medical image processing method according to claim 1, wherein, at the refraction point calculating step, a plurality of setting points are sequentially set on the outline, a length of a segment connecting two points which include one of the setting points at a center position having an equal length L/2 along the outline from the two points is compared with a length of another segment connecting two points which include another one of the setting points at a center position, a setting point corresponding to a segment having the smallest length is selected among the plurality of setting points, and the selected setting point is calculated as the refraction point.

* * * * *

UNITED STATES PATENT AND TRADEMARK OFFICE
CERTIFICATE OF CORRECTION

| | | |
|---|---|---|
| PATENT NO. | : 8,144,993 B2 | Page 1 of 1 |
| APPLICATION NO. | : 11/811263 | |
| DATED | : March 27, 2012 | |
| INVENTOR(S) | : Hirokazu Nishimura et al. | |

It is certified that error appears in the above-identified patent and that said Letters Patent is hereby corrected as shown below:

Column 28, line 5 (claim 9, line 2) should read: claim 3, wherein the isolated area detecting step has a deter- Signed and Sealed this
Thirty-first Day of July, 2012

David J. Kappos
*Director of the United States Patent and Trademark Office*